(12) United States Patent
Bewick-Sonntag et al.

(10) Patent No.: US 10,729,592 B2
(45) Date of Patent: Aug. 4, 2020

(54) ABSORBENT STRUCTURE

(71) Applicant: The Procter & Gamble Company, Cincinnati, OH (US)

(72) Inventors: Christopher Philip Bewick-Sonntag, Cincinnati, OH (US); Vito Carla, Cincinnati, OH (US); Wade Monroe Hubbard, Jr., Wyoming, OH (US); John Lee Hammons, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 446 days.

(21) Appl. No.: 15/344,177

(22) Filed: Nov. 4, 2016

(65) Prior Publication Data
US 2017/0119588 A1    May 4, 2017

Related U.S. Application Data

(60) Provisional application No. 62/251,057, filed on Nov. 4, 2015.

(51) Int. Cl.
*A61F 13/15*     (2006.01)
*A61L 15/28*     (2006.01)
*A61F 13/53*     (2006.01)

(52) U.S. Cl.
CPC ........ *A61F 13/15203* (2013.01); *A61F 13/53* (2013.01); *A61L 15/28* (2013.01); *A61F 2013/15544* (2013.01); *A61F 2013/530007* (2013.01); *A61F 2013/530233* (2013.01); *A61F 2013/530379* (2013.01); *A61F 2013/530817* (2013.01)

(58) Field of Classification Search
CPC .......... A61F 13/534; A61F 2013/15308; A61F 2013/15325; A61F 2013/1539; A61F 2013/530007; A61F 2013/530379; A61F 2013/530817
See application file for complete search history.

(56) References Cited

U.S. PATENT DOCUMENTS

| | | | |
|---|---|---|---|
| 1,035,758 A | 7/1919 | Thompson, Jr. et al. |
| 3,122,142 A | 2/1964 | Crowe, Jr. |
| 3,274,046 A | 9/1966 | Shannon et al. |
| 3,546,055 A | 12/1970 | Spertus |
| 3,617,594 A | 11/1971 | Willhy |
| 3,669,823 A | 6/1972 | Wood |
| 3,804,700 A | 4/1974 | Hoey |

(Continued)

FOREIGN PATENT DOCUMENTS

| | | |
|---|---|---|
| CA | 2250138 | 3/1997 |
| EP | 0278476 | 2/1988 |

(Continued)

OTHER PUBLICATIONS

PCT International Search Report, PCT/US2015/037943, dated Aug. 26, 2015, 9 pages.

(Continued)

*Primary Examiner* — Jacqueline F Stephens
(74) *Attorney, Agent, or Firm* — William E. Gallagher

(57) ABSTRACT

An absorbent structure comprising a single stratum exhibiting a Capillarity Work Potential greater than the Capillarity Work Potential trade-off Boundary.

17 Claims, 16 Drawing Sheets

(56) References Cited

U.S. PATENT DOCUMENTS

| | | |
|---|---|---|
| 3,815,601 A | 6/1974 | Schaefer |
| 3,884,000 A | 5/1975 | Faleij |
| 3,908,645 A | 9/1975 | Sandvig |
| 3,982,374 A | 9/1976 | Schaefer |
| 3,994,298 A | 11/1976 | Des Marais |
| 4,026,292 A | 5/1977 | Hutchins et al. |
| 4,055,184 A | 10/1977 | Karami |
| 4,061,145 A | 12/1977 | DesMarais |
| 4,096,303 A | 6/1978 | Doerfling |
| 4,357,386 A | 11/1982 | Luciano |
| 4,450,833 A | 5/1984 | Brooks |
| 4,473,611 A | 9/1984 | Haq |
| 4,535,021 A | 8/1985 | Friedrich |
| 4,606,958 A | 8/1986 | Haq et al. |
| 4,664,662 A | 5/1987 | Webster |
| 4,689,258 A | 8/1987 | Slosberg |
| 4,740,700 A | 4/1988 | Shaham |
| 4,758,466 A | 7/1988 | Dabi et al. |
| 4,865,596 A | 9/1989 | Weisman et al. |
| 5,147,345 A | 9/1992 | Young et al. |
| 5,160,345 A | 11/1992 | Bragg |
| 5,175,046 A | 12/1992 | Nguyen |
| 5,221,726 A | 6/1993 | Dabi et al. |
| 5,234,423 A | 8/1993 | Alemany et al. |
| 5,248,309 A | 9/1993 | Serbiak et al. |
| 5,260,345 A | 11/1993 | Desmarais et al. |
| 5,306,734 A | 4/1994 | Bass et al. |
| 5,328,935 A | 7/1994 | Van Phan et al. |
| 5,331,015 A | 7/1994 | DesMarais et al. |
| 5,338,766 A | 8/1994 | Phan et al. |
| 5,387,207 A * | 2/1995 | Dyer ............... A61F 5/4401 521/64 |
| 5,454,801 A | 10/1995 | Lauritzen |
| 5,487,736 A | 1/1996 | Van Phan |
| 5,536,264 A | 7/1996 | Hsueh et al. |
| 5,560,878 A | 10/1996 | Dragoo et al. |
| 5,713,881 A | 2/1998 | Rezai |
| 5,722,482 A | 3/1998 | Buckley |
| 5,817,704 A | 10/1998 | Shiveley et al. |
| 5,868,724 A | 2/1999 | Dierckes, Jr. et al. |
| 5,869,171 A * | 2/1999 | Shiveley ............ A61F 13/53 428/304.4 |
| 5,948,829 A | 9/1999 | Wallajapet et al. |
| 5,962,068 A | 10/1999 | Tsuchiya et al. |
| 6,083,211 A | 7/2000 | DesMarais |
| 6,103,645 A | 8/2000 | Chang et al. |
| 6,107,538 A | 8/2000 | Young et al. |
| 6,132,803 A | 10/2000 | Kelly et al. |
| 6,174,929 B1 | 1/2001 | Hahnle et al. |
| 6,183,587 B1 | 2/2001 | McFall et al. |
| 6,203,654 B1 | 3/2001 | McFall et al. |
| 6,261,679 B1 | 7/2001 | Chen et al. |
| 6,277,104 B1 | 8/2001 | Lasko et al. |
| 6,316,688 B1 | 11/2001 | Hammons et al. |
| 6,372,953 B1 * | 4/2002 | Young et al. ......... A61F 13/15 604/369 |
| 6,399,854 B1 | 6/2002 | Vartiainen |
| 6,410,820 B1 | 6/2002 | McFall et al. |
| 6,426,445 B1 | 7/2002 | Young et al. |
| 6,455,600 B1 | 9/2002 | Hahnle et al. |
| 6,475,199 B1 | 11/2002 | Gann et al. |
| 6,525,106 B1 | 2/2003 | DesMarais et al. |
| 6,551,295 B1 | 4/2003 | Schmidt et al. |
| 6,582,411 B1 | 6/2003 | Carstens et al. |
| 6,590,136 B1 | 7/2003 | Young et al. |
| 6,603,054 B2 | 8/2003 | Chen et al. |
| 6,642,430 B1 | 11/2003 | Busam et al. |
| 6,657,101 B1 | 12/2003 | Malmgren et al. |
| 6,664,439 B1 | 12/2003 | Arndt et al. |
| 6,673,057 B1 | 1/2004 | Ehrnsperger et al. |
| 6,673,981 B1 | 1/2004 | Strombom et al. |
| 6,689,935 B2 | 2/2004 | Chen et al. |
| 6,706,775 B2 | 3/2004 | Hermann et al. |
| 6,713,661 B1 | 3/2004 | Arndt et al. |
| 6,720,471 B1 | 4/2004 | Arndt et al. |
| 6,800,666 B2 | 10/2004 | Hahnle et al. |
| 6,811,842 B1 | 11/2004 | Ehrnsperger et al. |
| 6,855,424 B1 | 2/2005 | Thomas et al. |
| 6,943,200 B1 | 9/2005 | Corrand et al. |
| 6,969,548 B1 | 11/2005 | Goldfine |
| 6,989,005 B1 | 1/2006 | Lavon et al. |
| 7,056,404 B2 | 6/2006 | McFall et al. |
| 7,189,888 B2 | 3/2007 | Wang et al. |
| 7,235,708 B2 | 6/2007 | Guidotti et al. |
| 7,285,576 B2 | 10/2007 | Hyde et al. |
| 7,462,756 B2 | 12/2008 | Malowaniec |
| 7,850,672 B2 | 12/2010 | Guidotti et al. |
| 7,935,207 B2 | 5/2011 | Zhao et al. |
| 8,143,472 B1 | 3/2012 | Bragd et al. |
| 8,207,393 B2 | 6/2012 | Bach |
| 8,426,670 B2 | 4/2013 | Nagasuna et al. |
| 8,707,717 B2 | 4/2014 | Fox et al. |
| 8,708,723 B2 | 4/2014 | Stoltz |
| 8,906,404 B2 | 12/2014 | Wellings |
| 1,004,589 A1 | 8/2018 | Hubbard, Jr. |
| 2001/0041876 A1 | 11/2001 | Creagan et al. |
| 2001/0047456 A1 | 11/2001 | Schrobenhauzer et al. |
| 2002/0034911 A1 | 3/2002 | Tsuchiya et al. |
| 2002/0095132 A1 | 7/2002 | Ashton et al. |
| 2002/0132106 A1 | 9/2002 | Dyer et al. |
| 2003/0084788 A1 | 5/2003 | Fraser, Jr. |
| 2003/0134918 A1 | 7/2003 | Ko et al. |
| 2003/0181884 A1 | 9/2003 | Carstens et al. |
| 2003/0191204 A1 | 10/2003 | Hermann et al. |
| 2003/0211248 A1 | 11/2003 | Ko et al. |
| 2003/0220039 A1 | 11/2003 | Chen et al. |
| 2004/0054341 A1 | 3/2004 | Kellenberger et al. |
| 2004/0054342 A1 | 3/2004 | Newbill et al. |
| 2004/0121905 A1 | 6/2004 | Ranganathan et al. |
| 2004/0193129 A1 | 9/2004 | Guidotti et al. |
| 2004/0204554 A1 | 10/2004 | Ko et al. |
| 2004/0214961 A1 | 10/2004 | Gartner et al. |
| 2005/0087292 A1 | 4/2005 | McFall et al. |
| 2005/0136224 A1 | 6/2005 | Nickel et al. |
| 2005/0250866 A1 | 11/2005 | Champ et al. |
| 2005/0266230 A1 | 12/2005 | Hill et al. |
| 2006/0189240 A1 | 8/2006 | Taylor et al. |
| 2008/0076844 A1 | 3/2008 | Van Sumeren et al. |
| 2008/0217809 A1 | 9/2008 | Zhao et al. |
| 2008/0221538 A1 | 9/2008 | Zhao et al. |
| 2009/0270827 A1 | 10/2009 | Gundersen et al. |
| 2010/0162888 A1 | 7/2010 | Blucher et al. |
| 2010/0307665 A1 | 12/2010 | McCutchen |
| 2011/0070423 A1 | 3/2011 | Jayakody et al. |
| 2012/0001122 A1 | 1/2012 | Wattebled et al. |
| 2012/0108692 A1 | 5/2012 | Dyer |
| 2012/0201806 A1 | 8/2012 | Silverstein et al. |
| 2012/0237606 A1 | 9/2012 | Wellings |
| 2012/0296296 A1 | 11/2012 | Dicintio et al. |
| 2012/0302440 A1 | 11/2012 | Theliander et al. |
| 2013/0079741 A1 | 3/2013 | Nakashita et al. |
| 2014/0050886 A1 | 2/2014 | Burgin et al. |
| 2014/0228796 A1 | 8/2014 | Burvall et al. |
| 2014/0295134 A1 | 10/2014 | Wood et al. |
| 2014/0295135 A1 | 10/2014 | Thompson, Jr. et al. |
| 2015/0119837 A1 | 4/2015 | Thompson, Jr. et al. |
| 2015/0245957 A1 | 9/2015 | Hashino et al. |
| 2015/0374876 A1 | 12/2015 | Hubbard, Jr. |

FOREIGN PATENT DOCUMENTS

| | | |
|---|---|---|
| EP | 0794751 | 11/1995 |
| EP | 1061966 | 3/1999 |
| EP | 1267769 | 1/2003 |
| EP | 1605881 | 1/2004 |
| EP | 1139951 | 10/2004 |
| EP | 1358894 | 11/2013 |
| GB | 1570485 | 7/1980 |
| GB | 2326828 | 1/1999 |
| JP | 2013180171 A | 9/2013 |
| WO | WO9611714 | 4/1996 |
| WO | WO9945878 | 9/1999 |
| WO | WO9947184 | 9/1999 |
| WO | WO9955269 | 11/1999 |

(56) References Cited

FOREIGN PATENT DOCUMENTS

| WO | WO0000138 | 1/2000 |
|----|-----------|--------|
| WO | WO0000136 | 12/2000 |
| WO | WO0059438 | 12/2000 |
| WO | WO0078369 | 12/2000 |
| WO | WO2001068022 | 9/2001 |
| WO | WO2003026707 | 10/2003 |
| WO | WO2004084784 | 10/2004 |
| WO | WO2004084785 | 10/2004 |
| WO | WO2013180937 | 12/2013 |

OTHER PUBLICATIONS

PCT International Search Report, PCT/US2015/029199, dated Jul. 21, 2015, 12 pages.
PCT International Search Report, PCT/US2015/032154, dated Aug. 26, 2015, 10 pages.
PCT International Search Report, PCT/US2016/060568, dated Feb. 20, 2017, 11 pages.
All Office Actions, U.S. Appl. No. 14/704,110.
All Office Actions, U.S. Appl. No. 14/715,984.
All Office Actions, U.S. Appl. No. 14/750,596.
All Office Actions, U.S. Appl. No. 15/084,902.
All Office Actions, U.S. Appl. No. 15/344,050.
All Office Actions, U.S. Appl. No. 15/344,090.
All Office Actions, U.S. Appl. No. 15/344,117.
All Office Actions, U.S. Appl. No. 15/344,177.
All Office Actions, U.S. Appl. No. 15/344,255.
All Office Actions, U.S. Appl. No. 15/344,292.

* cited by examiner

ABSORBENT STRUCTURE

FIELD OF THE INVENTION

The present invention relates to absorbent structures useful in absorbent articles such as diapers, incontinent briefs, training pants, diaper holders and liners, sanitary hygiene garments, and the like. Specifically, the present invention relates to an absorbent structure that exhibits desirable consumer properties.

BACKGROUND OF THE INVENTION

Absorbent articles for the absorption of fluids aim to rapidly absorb fluids so that they are not left in contact with the user. Conventional Porous Media (PM) structures and super absorbent polymers (SAP) utilized as acquisition and storage layers in the hygiene product industry show a known trade-off between driving force for fluid acquisition (capillary suction) and resistance to the flow (inverse of permeability). This is due to the underlying physics behind flow into the desired material, which can be effectively described by statistical percolation theories.

Ultimately, the material structure is responsible for both driving force and resistance to flow in such a way that whenever the structure presents high surface/volume ratios the capillary suction increases but the permeability decreases, because the flow becomes more tortuous. Conversely, whenever the ratio surface to volume is low in a porous material, then the resistance to flow is reduced (high permeability) at the expenses of the capillary suction.

This dichotomy is effectively represented by a single capillary tube model. By increasing the radius of the capillary, one can significantly speed up the capillary rise against gravity (representing our acquisition process) at the expense of the driving force (capillary pressure). This is shown as reduced equilibrium pressure (which in the case of absorbent products translates to lower rewet pressure and hence less secure storage). On the other hand, decreasing the capillary radius allows to securely store more fluid against pressure at the expense of the speed of acquisition as the capillary rise process becomes slower.

As such there exists a need to create an absorbent structure that breaks the tradeoff between capillarity and permeability in a single stratum to create a product that exhibits both high capillarity and high permeability.

SUMMARY OF THE INVENTION

An absorbent structure comprising a single stratum exhibiting a Capillarity Work Potential greater than the Capillarity Work Potential trade-off Boundary is described.

An absorbent structure comprising a single stratum exhibiting a permeability greater than the Capillarity Work Potential trade-off Boundary for a given Capillary Work Potential is also described.

An absorbent structure comprising a single stratum exhibiting a Capillarity Work Potential for a fixed permeability that is greater than the Capillarity Work Potential trade-off Boundary and less than 20 times the Capillary Work Potential trade-off; and a permeability greater than the Capillarity Work Potential trade-off Boundary for a given Capillary Work Potential is also described.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
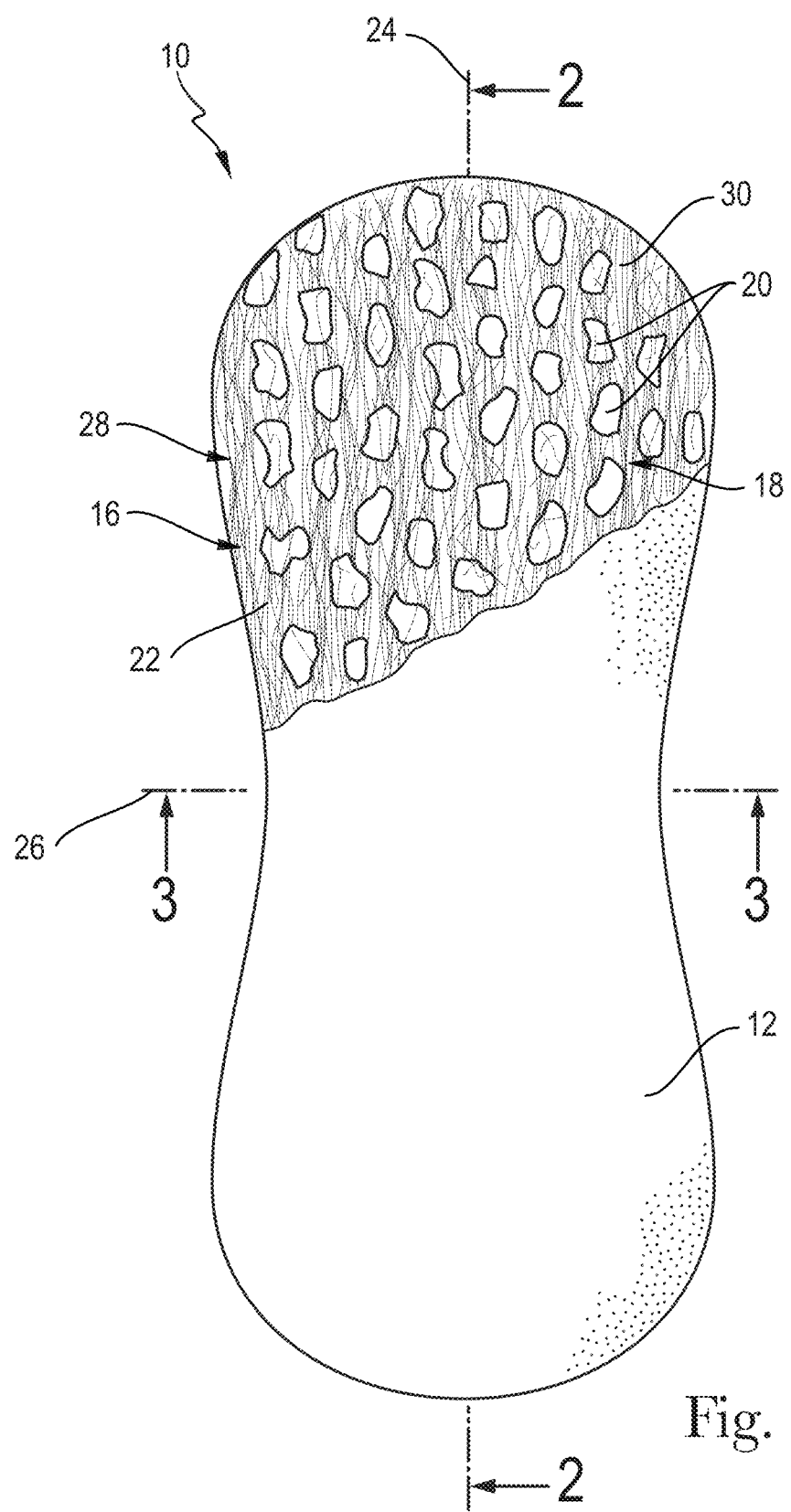
FIG. 1 is a top view of an absorbent article.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

In the following description the term "cellulose fibers" is used. Cellulose fibers comprise naturally occurring fibers based on cellulose, such as, for example cotton, linen, etc. Wood pulp fibers are one example of cellulose fibers according to the present invention. Man-made fibers derived from cellulose, such as regenerated cellulose, e.g. viscose or partially or fully acetylated cellulose derivatives (e.g. cellulose acetate or triacetate), are also considered as cellulose fibers according to the present invention.

The term "disposable" is used herein to describe articles, which are not intended to be laundered or otherwise restored or reused as an article (i.e. they are intended to be discarded after a single use and possibly to be recycled, composted or otherwise disposed of in an environmentally compatible manner). The absorbent article comprising an absorbent structure according to the present invention can be for example a sanitary napkin, a panty liner, an adult incontinence product, a diaper, or any other product designed to absorb a bodily exudate. The absorbent structure of the present invention will be herein described in the context of a typical absorbent article, such as, for example, a sanitary napkin. Typically, such articles may comprise a liquid pervious topsheet, a backsheet and an absorbent core intermediate the topsheet and the backsheet.

As used herein, an "enrobeable element" refers to an element that may be enrobed by the foam. The enrobeable element may be, for example, a fiber, a group of fibers, a tuft, or a section of a film between two apertures. It is understood that other elements are contemplated by the present invention.

A "fiber" as used herein, refers to any material that may be part of a fibrous structure. Fibers may be natural or synthetic. Fibers may be absorbent or non-absorbent.

A "fibrous structure" as used herein, refers to materials which may be broken into one or more fibers. A fibrous structure can be absorbent or adsorbent. A fibrous structure may exhibit capillary action as well as porosity and permeability.

As used herein, the term "immobilize" refers to the reduction or the elimination of movement or motion.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter. Thereafter, the meltblown fibers are carried by the high velocity gas stream and are deposited on a collecting surface, often while still tacky, to form a web of randomly dispersed meltblown fibers.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "non-round fibers" describes fibers having a non-round cross-section, and includes "shaped fibers" and "capillary channel fibers." Such fibers may be solid or hollow, and they may be tri-lobal, delta-shaped, and may be fibers having capillary channels on their outer surfaces. The capillary channels may be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, Tenn. T-401 fiber is a polyethylene terephthalate (PET polyester).

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, electro-spinning, meltblowing processes, spunbonding processes, spunlacing processes, hydroentangling, airlaying, and bonded carded web processes, including carded thermal bonding. The basis weight of nonwoven fabrics is usually expressed in grams per square meter (gsm). The basis weight of the laminate web is the combined basis weight of the constituent layers and any other added components. Fiber diameters are usually expressed in microns; fiber size may also be expressed in denier, which is a unit of weight per length of fiber. The basis weight of laminate webs suitable for use in an article of the present invention may range from about 10 gsm to about 100 gsm, depending on the ultimate use of the web.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "recovery energy" relates to an indicator of how well an absorbent structure or absorbent product may retain or regain is original shape. More specifically, "recovery energy" is a measure of the amount of work the absorbent structure or the absorbent product will perform against the consumer's body and/or garment following compression. Without being bound by theory, the upper limit for recovery energy should be the compressive energy i.e. a fully recovered product when removed from the consumer's body/garment. Dry recovery energy for between 1 and 20 cycles should be less than 250% the dry compressive energy of a new product.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample size of at least 10 fibers) larger than 7 microns, and more particularly, between about 10 and 40 microns.

As used herein, a "strata" or "stratum" relates to one or more layers wherein the components within the layer are intimately combined without the necessity of an adhesive, pressure bonds, heat welds, a combination of pressure and heat bonding, ultrasonic bonding, or similar methods of bonding known in the art such that individual components may not be wholly separated from the stratum without affecting the physical structure of the other components. The skilled artisan should understand that while separate bonding is unnecessary between the strata, bonding techniques could be employed to provide additional integrity depending on the intended use.

As used herein, a "tuft" or chad relates to discrete integral extensions of the fibers of a nonwoven web. Each tuft may comprise a plurality of looped, aligned fibers extending outwardly from the surface of the web. Each tuft may comprise a plurality of non-looped fibers that extend outwardly from the surface of the web. Each tuft may comprise a plurality of fibers which are integral extensions of the fibers of two or more integrated nonwoven webs.

As used herein, a "usage cycle" relates to the duration of use of the absorbent structure as it transitions from a dry state to a saturated wet state.

While particular embodiments of the present invention have been illustrated and described, it would be obvious to those skilled in the art that various other changes and modifications may be made without departing from the spirit and scope of the invention.

General Summary

The present invention relates to an absorbent structure that is flexible and maintains its resiliency while in use. The absorbent structure is a single stratum that exhibits a Capillary Work Potential (CWP) that is greater than the Capillary Work Potential quantified along the trade-off (CWP$_{t-o}$) boundary.

The absorbent structure single stratum may comprise one or more absorbent layers. The absorbent structure single stratum may be a heterogeneous mass.

The absorbent core structure may comprise a heterogeneous mass layer as those described in U.S. patent application No. 61/988,565, filed May 5, 2014; U.S. patent application No. 62/115,921, filed Feb. 13, 2015; or U.S. patent application No. 62/018,212. The heterogeneous mass layer has a depth, a width, and a height.

The absorbent structure single stratum may be combined with other absorbent core elements such as those described in U.S. Pat. No. 8,263,820 issued Sep. 11, 2012 and U.S. Pat. No. 8,124,827 issued Feb. 28, 2012 to form an absorbent structure.

The absorbent core structure may comprise a substrate and superabsorbent polymer layer as those described in U.S. application Ser. No. 12/718,244 published on Sep. 9, 2010; U.S. application Ser. No. 12/754,935 published on Oct. 14, 2010; or U.S. Pat. No. 8,674,169 issued on Mar. 18, 2014.

The absorbent structure may have a substrate layer. The substrate layer of the absorbent structure may advantageously comprise a fibrous material substantially free of cellulose fibers. By saying that a layer of the absorbent core is "substantially free" of cellulose fibers, it is meant in the context of the present invention that the layer should not comprise any significant amount of cellulose fibers within its inner structure. While cellulose fibers which may be present at an outer surface of the specified layer, for example at the interface between the specified layer and an adjacent one, which could be for example an outer layer wrapping the core, in some cases may accidentally and slightly penetrate the structure of the specified layer, such shall not be considered significant. Significant amounts may correspond to less than 10% by weight, less than 5% by weight, less than 3% by weight, or less than 1% by weight, based on the dry weight of the specified layer of the absorbent core. The substrate layer may also have a basis weight from 25 g/m$^2$ to 120 g/m$^2$, or from 35 g/m$^2$ to 90 g/m$^2$.

The absorbent structure may have a thermoplastic layer of thermoplastic material. The thermoplastic material may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic composition may be a hot melt adhesive comprising at least one thermoplastic polymer in combination with other thermoplastic diluents such as tackifying resins, plasticizers and additives such as antioxidants.

The thermoplastic polymer may have typically a molecular weight (Mw) of more than 10,000 and a glass transition temperature (Tg) usually below room temperature. Typical concentrations of the polymer in a hot melt are in the range of 20-40% by weight. A wide variety of thermoplastic polymers may be suitable for use in the present invention. Such thermoplastic polymers may be typically water insensitive. Exemplary polymers may be (styrenic) block copolymers including A-B-A triblock structures, A-B diblock structures and (A-B)n radial block copolymer structures wherein the A blocks may be non-elastomeric polymer blocks, typically comprising polystyrene, and the B blocks may be unsaturated conjugated diene or (partly) hydrogenated versions of such. The B block may be typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer may be polymerized with ethylene to make a copolymer, terpolymer or higher order polymer. Also applicable may be amorphous polyolefins or amorphous polyalphaolefins (APAO) which are homopolymers, copolymers or terpolymers of C2 to C8 alphaolefins.

The resin may typically have a Mw below 5,000 and a Tg usually above room temperature, typical concentrations of the resin in a hot melt may be in the range of 30-60%. The plasticizer has a low Mw of typically less than 1,000 and a Tg below room temperature, a typical concentration is 0-15%.

The thermoplastic material, typically a hotmelt adhesive, may be present in the form of fibers throughout the core, being provided with known means, i.e. the adhesive may be fiberized. Typically, the fibers may have an average thickness of 1-100 micrometer and an average length of 5 mm to 50 cm. In particular the layer of thermoplastic material, typically e.g. a hot melt adhesive, may be provided such as to comprise a net-like structure.

To improve the adhesiveness of the thermoplastic material to the substrate layer or to any other layer, in particular any other non-woven layer, such layers may be pre-treated with an auxiliary adhesive.

The absorbent structure may have absorbent polymer material. Without wishing to be bound by theory it is believed that such material, even in the swollen state, i.e. when liquid has been absorbed, does not substantially obstruct the liquid flow throughout the material, particularly when further the permeability of said material, as expressed by the saline flow conductivity (SFC) of the absorbent polymer material, is greater than 10, 20, 30 or 40 SFC-units, where 1 SFC unit is $1\times10^{-7}$ (cm$^3$×s)/g. Saline flow conductivity is a parameter well recognized in the art and is to be measured in accordance with the test disclosed in EP 752 892 B.

The absorbent structure may be a heterogeneous mass. The heterogeneous mass has a depth, a width, and a height. The absorbent structure may be used as any part of an absorbent article including, for example, a part of an absorbent core, as an absorbent core, and/or as a topsheet for absorbent articles such as sanitary napkins, panty liners, tampons, interlabial devices, wound dressings, diapers, adult incontinence articles, and the like, which are intended for the absorption of body fluids, such as menses or blood or vaginal discharges or urine. The absorbent structure may be used in any product utilized to absorb and retain a fluid including surface wipes. The absorbent structure may be used as a paper towel. Exemplary absorbent articles in the context of the present invention are disposable absorbent articles.

The absorbent structure single stratum may be a heterogeneous mass comprising enrobeable elements and one or more portions of foam pieces. The discrete portions of foam pieces are open-celled foam. The foam may be a High Internal Phase Emulsion (HIPE) foam.

The absorbent structure single stratum may be an absorbent core for an absorbent article wherein the absorbent core comprises a heterogeneous mass comprising fibers and one or more discrete portions of foam that are immobilized in the heterogeneous mass or may be combined with other layers to form an absorbent core.

In the following description of the invention, the surface of the article, or of each component thereof, which in use faces in the direction of the wearer is called wearer-facing surface. Conversely, the surface facing in use in the direction of the garment is called garment-facing surface. The absorbent article of the present invention, as well as any element thereof, such as, for example the absorbent core, has therefore a wearer-facing surface and a garment-facing surface.

The present invention relates to an absorbent structure single stratum that contains one or more discrete open-cell foam pieces foams that are integrated into a heterogeneous mass comprising one or more enrobeable elements integrated into the one or more open-cell foams such that the two may be intertwined.

The open-cell foam pieces may comprise between 1% of the heterogeneous mass by volume to 99% of the heterogeneous mass by volume, such as, for example, 5% by volume, 10% by volume, 15% by volume, 20% by volume, 25% by volume, 30% by volume, 35% by volume, 40% by volume, 45% by volume, 50% by volume, 55% by volume, 60% by volume, 65% by volume, 70% by volume, 75% by volume, 80% by volume, 85% by volume, 90% by volume, or 95% by volume.

The heterogeneous mass may have void space found between the enrobeable elements, between the enrobeable elements and the enrobed elements, and between enrobed elements. The void space may contain a gas such as air. The void space may represent between 1% and 95% of the total volume for a fixed amount of volume of the heterogeneous mass, such as, for example, 5%, 10%, 15%, 20%, 25%, 30%, 35%, 40%, 45%, 50%, 55%, 60%, 65%, 70%, 75%, 80%, 85%, 90% of the total volume for a fixed amount of volume of the heterogeneous mass.

The combination of open-cell foam pieces and void space within the heterogeneous mass may exhibit an absorbency of between 10 g/g to 200 g/g of the, such as for example, between 20 g/g and 190 g/g of the heterogeneous mass, such as, for example 30 g/g, 40 g/g, 60 g/g, 80 g/g, 100 g/g, 120 g/g, 140 g/g 160 g/g 180 g/g or 190 g/g of the heterogeneous mass. Absorbency may be quantified according to the EDANA Nonwoven Absorption method 10.4-02.

The open-cell foam pieces are discrete foam pieces intertwined within and throughout a heterogeneous mass such that the open-cell foam enrobes one or more of the enrobeable elements such as, for example, fibers within the mass. The open-cell foam may be polymerized around the enrobeable elements.

A discrete open-cell foam piece may enrobe more than one enrobeable element. The enrobeable elements may be enrobed together as a bunch. Alternatively, more than one enrobeable element may be enrobed by the discrete open-cell foam piece without contacting another enrobeable element.

A discrete open-cell foam piece may be immobilized such that the discrete open-cell foam piece does not change location within the heterogeneous mass during use of the absorbent structure.

A plurality of discrete open-cell foams may be immobilized such that the discrete open-cell foam pieces do not change location within the heterogeneous mass during use of the absorbent structure.

One or more discrete foam pieces may be immobilized within the heterogeneous mass such that the one or more discrete foam pieces do not change location after being spun at 300 rotations per minute for 30 seconds.

The open-cell foam pieces may be discrete. Open-cell foam pieces are considered discrete in that they are not continuous throughout the entire heterogeneous mass. Not continuous throughout the entire heterogeneous mass represents that at any given point in the heterogeneous mass, the open-cell absorbent foam is not continuous in at least one of the cross sections of a longitudinal, a vertical, and a lateral plane of the heterogeneous mass. The absorbent foam may or may not be continuous in the lateral and the vertical planes of the cross section for a given point in the heterogeneous mass. The absorbent foam may or may not be continuous in the longitudinal and the vertical planes of the cross section for a given point in the heterogeneous mass. The absorbent foam may or may not be continuous in the longitudinal and the lateral planes of the cross section for a given point in the heterogeneous mass.

When the open-cell foam is not continuous in at least one of the cross sections of the longitudinal, the vertical, and the lateral plane of the heterogeneous mass, one or both of either the enrobeable elements or the open-cell foam pieces may be bi-continuous throughout the heterogeneous mass.

The open-cell foam pieces may be located at any point in the heterogeneous mass. A foam piece may be surrounded by the elements that make up the enrobeable elements. A foam piece may be located on the outer perimeter of the heterogeneous mass such that only a portion of the foam piece is entangled with the elements of the heterogeneous mass.

The open-cell foam pieces may expand upon being contacted by a fluid to form a channel of discrete open-cell foam pieces. The open-cell foam pieces may or may not be in contact prior to being expanded by a fluid.

An open-celled foam may be integrated onto the enrobeable elements prior to being polymerized. The open-cell foam pieces may be partially polymerized prior to being impregnated into or onto the enrobeable elements such that they become intertwined. After being impregnated into or onto the enrobeable elements, the open-celled foam in either a liquid or solid state are polymerized to form one or more open-cell foam pieces. The open-celled foam may be polymerized using any known method including, for example, heat, UV, and infrared. Following the polymerization of a water in oil open-cell foam emulsion, the resulting open-cell foam is saturated with aqueous phase that needs to be removed to obtain a substantially dry open-cell foam. Removal of the saturated aqueous phase or dewatering may occur using nip rollers, and vacuum. Utilizing a nip roller may also reduce the thickness of the heterogeneous mass such that the heterogeneous mass will remain thin until the open-cell foam pieces entwined in the heterogeneous mass are exposed to fluid.

Dependent upon the desired foam density, polymer composition, specific surface area, or pore-size (also referred to as cell size), the open-celled foam may be made with different chemical composition, physical properties, or both. For instance, dependent upon the chemical composition, an open-celled foam may have a density of 0.0010 g/cc to about 0.25 g/cc, or from 0.002 g/cc to about 0.2 g/cc, or from about 0.005 g/cc to about 0.15 g/cc, or from about 0.01 g/cc to about 0.1 g/cc, or from about 0.02 g/cc to about 0.08 g/cc, or about 0.04 g/cc.

Open-cell foam pore-sizes may range in average diameter of from 1 to 800 μm, such as, for example, between 50 and 700 μm, between 100 and 600 μm, between 200 and 500 μm, between 300 and 400 μm.

The foam pieces may have a relatively uniform cell size. For example, the average cell size on one major surface may be about the same or vary by no greater than 10% as compared to the opposing major surface. The average cell size of one major surface of the foam may differ from the opposing surface. For example, in the foaming of a thermosetting material it is not uncommon for a portion of the cells at the bottom of the cell structure to collapse resulting in a lower average cell size on one surface. The cell size may be determined based upon the method found below.

The foams produced from the present invention are relatively open-celled. This refers to the individual cells or pores of the foam being in substantially unobstructed communication with adjoining cells. The cells in such substantially open-celled foam structures have intercellular openings or windows that are large enough to permit ready fluid transfer from one cell to another within the foam structure. For purpose of the present invention, a foam is considered "open-celled" if at least about 80% of the cells in the foam that are at least 1 μm in average diameter size are in fluid communication with at least one adjoining cell.

In addition to being open-celled, the foams may be sufficiently hydrophilic to permit the foam to absorb aqueous fluids, for example the internal surfaces of a foam may be rendered hydrophilic by residual hydrophilizing surfactants or salts left in the foam following polymerization, by selected post-polymerization foam treatment procedures (as described hereafter), or combinations of both.

For example when used in certain absorbent articles, an open-cell foam may be flexible and exhibit an appropriate glass transition temperature (Tg). The Tg represents the midpoint of the transition between the glassy and rubbery states of the polymer.

The Tg of a region may be less than about 200° C. for foams used at about ambient temperature conditions, or less than about 90° C. The Tg may be less than 50° C.

The open-cell foam pieces may be distributed in any suitable manner throughout the heterogeneous mass. The open-cell foam pieces may be profiled along the vertical axis such that smaller pieces are located above larger pieces. Alternatively, the pieces may be profiled such that smaller pieces are below larger pieces. The open-cell pieces may be profiled along a vertical axis such that they alternate in size along the axis.

The open-cell foam pieces may be profiled along the longitudinal axis such that smaller pieces are located in front of larger pieces. Alternatively, the pieces may be profiled such that smaller pieces are behind larger pieces. The open-cell pieces may be profiled along a longitudinal axis such that they alternate in size along the axis.

The open-cell foam pieces may be profiled along the lateral axis such the size of the pieces goes from small to large or from large to small along the lateral axis. Alternatively, the open-cell pieces may be profiled along a lateral axis such that they alternate in size along the axis.

The open-cell foam pieces may be profiled along any one of the longitudinal, lateral, or vertical axis based on one or more characteristics of the open-cell foam pieces. Characteristics by which the open-cell foam pieces may be profiled within the heterogeneous mass may include, for example, absorbency, density, cell size, and combinations thereof.

The open-cell foam pieces may be profiled along any one of the longitudinal, lateral, or vertical axis based on the composition of the open-cell foam. The open-cell foam pieces may have one composition exhibiting desirable characteristics in the front of the heterogeneous mass and a different composition in the back of the heterogeneous mass designed to exhibit different characteristics. The profiling of the open-cell foam pieces may be either symmetric or asymmetric about any of the prior mentioned axes or orientations.

The open-cell foam pieces may be distributed along the longitudinal and lateral axis of the heterogeneous mass in any suitable form. The open-cell foam pieces may be distributed in a manner that forms a design or shape when viewed from a top planar view. The open-cell foam pieces may be distributed in a manner that forms stripes, ellipticals, squares, or any other known shape or pattern.

The distribution may be optimized dependent on the intended use of the heterogeneous mass. For example, a different distribution may be chosen for the absorption of aqueous fluids such as urine when used in a diaper or water when used in a paper towel versus for the absorption of a proteinaceous fluid such as menses. Further, the distribution may be optimized for uses such as dosing an active or to use the foam as a reinforcing element.

Different types of foams may be used in one heterogeneous mass. For example, some of the foam pieces may be polymerized HIPE while other pieces may be made from polyurethane. The pieces may be located at specific locations within the mass based on their properties to optimize the performance of the heterogeneous mass.

The foam pieces may be similar in composition yet exhibit different properties. For example, using HIPE foam, some foam pieces may be thin until wet while others may have been expanded within the heterogeneous mass.

The foam pieces and enrobeable elements may be selected to complement each other. For example, a foam that exhibits high permeability with low capillarity may enrobe an element that exhibits high capillarity to wick the fluid through the heterogeneous mass. It is understood that other combinations may be possible wherein the foam pieces complement each other or wherein the foam pieces and enrobeable elements both exhibit similar properties.

Profiling may occur using more than one heterogeneous mass with each heterogeneous mass having one or more types of foam pieces. The plurality of heterogeneous masses may be layered so that the foam is profiled along any one of the longitudinal, lateral, or vertical axis based on one or more characteristics of the open-cell foam pieces for an overall product that contains the plurality of heterogeneous masses. Further, each heterogeneous mass may have a different enrobeable element to which the foam is attached. For example, a first heterogeneous mass may have foam particles enrobing a nonwoven while a second heterogeneous mass adjacent the first heterogeneous mass may have foam particles enrobing a film or one surface of a film.

The open-celled foam may be a thermoset polymeric foam made from the polymerization of a High Internal Phase Emulsion (HIPE), also referred to as a polyHIPE. To form a HIPE, an aqueous phase and an oil phase are combined in a ratio between about 8:1 and 140:1. The aqueous phase to oil phase ratio may be between about 10:1 and about 75:1, and the aqueous phase to oil phase ratio may be between about 13:1 and about 65:1. This is termed the "water-to-oil"

or W:O ratio and may be used to determine the density of the resulting polyHIPE foam. As discussed, the oil phase may contain one or more of monomers, comonomers, photoinitiators, crosslinkers, and emulsifiers, as well as optional components. The water phase may contain water and one or more components such as electrolyte, initiator, or optional components.

The open-cell foam may be formed from the combined aqueous and oil phases by subjecting these combined phases to shear agitation in a mixing chamber or mixing zone. The combined aqueous and oil phases are subjected to shear agitation to produce a stable HIPE having aqueous droplets of the desired size. An initiator may be present in the aqueous phase, or an initiator may be introduced during the foam making process, or after the HIPE has been formed. The emulsion making process produces a HIPE where the aqueous phase droplets are dispersed to such an extent that the resulting HIPE foam will have the desired structural characteristics. Emulsification of the aqueous and oil phase combination in the mixing zone may involve the use of a mixing or agitation device such as an impeller, by passing the combined aqueous and oil phases through a series of static mixers at a rate necessary to impart the requisite shear, or combinations of both. Once formed, the HIPE may then be withdrawn or pumped from the mixing zone. One method for forming HIPEs using a continuous process is described in U.S. Pat. No. 5,149,720 (DesMarais et al), issued Sep. 22, 1992; U.S. Pat. No. 5,827,909 (DesMarais) issued Oct. 27, 1998; and U.S. Pat. No. 6,369,121 (Catalfamo et al.) issued Apr. 9, 2002.

The emulsion may be withdrawn or pumped from the mixing zone and impregnated into or onto a mass prior to being fully polymerized. Once fully polymerized, the foam pieces and the elements are intertwined such that discrete foam pieces are bisected by the elements comprising the mass and such that parts of discrete foam pieces enrobe portions of one or more of the elements comprising the heterogeneous mass.

Following polymerization, the resulting foam pieces are saturated with aqueous phase that needs to be removed to obtain substantially dry foam pieces. Foam pieces may be squeezed free of most of the aqueous phase by using compression, for example by running the heterogeneous mass comprising the foam pieces through one or more pairs of nip rollers. The nip rollers may be positioned such that they squeeze the aqueous phase out of the foam pieces. The nip rollers may be porous and have a vacuum applied from the inside such that they assist in drawing aqueous phase out of the foam pieces. Nip rollers may be positioned in pairs, such that a first nip roller is located above a liquid permeable belt, such as a belt having pores or composed of a mesh-like material and a second opposing nip roller facing the first nip roller and located below the liquid permeable belt. One of the pair, for example the first nip roller may be pressurized while the other, for example the second nip roller, may be evacuated, so as to both blow and draw the aqueous phase out the of the foam. The nip rollers may also be heated to assist in removing the aqueous phase. Nip rollers may be applied to non-rigid foams, that is, foams whose walls would not be destroyed by compressing the foam pieces.

In place of or in combination with nip rollers, the aqueous phase may be removed by sending the foam pieces through a drying zone where it is heated, exposed to a vacuum, or a combination of heat and vacuum exposure. Heat may be applied, for example, by running the foam though a forced air oven, IR oven, microwave oven or radiowave oven. The extent to which a foam is dried depends on the application. Greater than 50% of the aqueous phase may be removed. Greater than 90%, and in still other embodiments greater than 95% of the aqueous phase may be removed during the drying process.

Open-cell foam may be produced from the polymerization of the monomers having a continuous oil phase of a High Internal Phase Emulsion (HIPE). The HIPE may have two phases. One phase is a continuous oil phase having monomers that are polymerized to form a HIPE foam and an emulsifier to help stabilize the HIPE. The oil phase may also include one or more photoinitiators. The monomer component may be present in an amount of from about 80% to about 99%, and in certain embodiments from about 85% to about 95% by weight of the oil phase. The emulsifier component, which is soluble in the oil phase and suitable for forming a stable water-in-oil emulsion may be present in the oil phase in an amount of from about 1% to about 20% by weight of the oil phase. The emulsion may be formed at an emulsification temperature of from about 10° C. to about 130° C. and in certain embodiments from about 50° C. to about 100° C.

In general, the monomers will include from about 20% to about 97% by weight of the oil phase at least one substantially water-insoluble monofunctional alkyl acrylate or alkyl methacrylate. For example, monomers of this type may include $C_4$-$C_{18}$ alkyl acrylates and $C_2$-$C_{18}$ methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also have from about 2% to about 40%, and in certain embodiments from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type may have monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,12-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate:acrylate group in the mixed crosslinker may be varied from 50:50 to any other ratio as needed.

Any third substantially water-insoluble comonomer may be added to the oil phase in weight percentages of from about 0% to about 15% by weight of the oil phase, in certain embodiments from about 2% to about 8%, to modify properties of the HIPE foams. "Toughening" monomers may be desired which impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028 (Dyer) issued Dec. 12, 2000. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers may be used to slow down the polymerization rate of a HIPE. Examples of monomers of this type may have styrene and vinyl chloride.

The oil phase may further contain an emulsifier used for stabilizing the HIPE. Emulsifiers used in a HIPE may include: (a) sorbitan monoesters of branched $C_{16}$-$C_{24}$ fatty acids; linear unsaturated $C_{16}$-$C_{22}$ fatty acids; and linear saturated $C_{12}$-$C_{14}$ fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched $C_{16}$-$C_{24}$ fatty acids, linear unsaturated $C_{16}$-$C_{22}$ fatty acids, or linear saturated $C_{12}$-$C_{14}$ fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched $C_{16}$-$C_{24}$ alcohols, linear unsaturated $C_{16}$-$C_{22}$ alcohols, and linear saturated $C_{12}$-$C_{14}$ alcohols, and mixtures of these emulsifiers. See U.S. Pat. No. 5,287,207 (Dyer et al.), issued Feb. 7, 1995 and U.S. Pat. No. 5,500,451 (Goldman et al.) issued Mar. 19, 1996. Another emulsifier that may be used is polyglycerol succinate (PGS), which is formed from an alkyl succinate, glycerol, and triglycerol.

Such emulsifiers, and combinations thereof, may be added to the oil phase so that they may have between about 1% and about 20%, in certain embodiments from about 2% to about 15%, and in certain other embodiments from about 3% to about 12% by weight of the oil phase. Coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain $C_{12}$-$C_{22}$ dialiphatic quaternary ammonium salts, short chain $C_1$-$C_4$ dialiphatic quaternary ammonium salts, long chain $C_{12}$-$C_{22}$ dialkoyl(alkenoyl)-2-hydroxyethyl, short chain $C_1$-$C_4$ dialiphatic quaternary ammonium salts, long chain $C_{12}$-$C_{22}$ dialiphatic imidazolinium quaternary ammonium salts, short chain $C_1$-$C_4$ dialiphatic imidazolinium quaternary ammonium salts, long chain $C_{12}$-$C_{22}$ monoaliphatic benzyl quaternary ammonium salts, long chain $C_{12}$-$C_{22}$ dialkoyl(alkenoyl)-2-aminoethyl, short chain $C_1$-$C_4$ monoaliphatic benzyl quaternary ammonium salts, short chain $C_1$-$C_4$ monohydroxyaliphatic quaternary ammonium salts. Ditallow dimethyl ammonium methyl sulfate (DTDMAMS) may be used as a coemulsifier.

The oil phase may comprise a photoinitiator at between about 0.05% and about 10%, and in certain embodiments between about 0.2% and about 10% by weight of the oil phase. Lower amounts of photoinitiator allow light to better penetrate the HIPE foam, which may provide for polymerization deeper into the HIPE foam. However, if polymerization is done in an oxygen-containing environment, there should be enough photoinitiator to initiate the polymerization and overcome oxygen inhibition. Photoinitiators may respond rapidly and efficiently to a light source with the production of radicals, cations, and other species that are capable of initiating a polymerization reaction. The photoinitiators used in the present invention may absorb UV light at wavelengths of about 200 nanometers (nm) to about 800 nm, in certain embodiments about 200 nm to about 350 nm. If the photoinitiator is in the oil phase, suitable types of oil-soluble photoinitiators include benzyl ketals, α-hydroxyalkyl phenones, α-amino alkyl phenones, and acylphospine oxides. Examples of photoinitiators include 2,4,6-[trimethylbenzoyldiphosphine] oxide in combination with 2-hydroxy-2-methyl-1-phenylpropan-1-one (50:50 blend of the two is sold by Ciba Speciality Chemicals, Ludwigshafen, Germany as DAROCUR® 4265); benzyl dimethyl ketal (sold by Ciba Geigy as IRGACURE 651); α-,α-dimethoxy-α-hydroxy acetophenone (sold by Ciba Speciality Chemicals as DAROCUR® 1173); 2-methyl-1-[4-(methyl thio) phenyl]-2-morpholino-propan-1-one (sold by Ciba Speciality Chemicals as IRGACURE® 907); 1-hydroxycyclohexyl-phenyl ketone (sold by Ciba Speciality Chemicals as IRGACURE® 184); bis(2,4,6-trimethylbenzoyl)-phenyl-phosphineoxide (sold by Ciba Speciality Chemicals as IRGACURE 819); diethoxyacetophenone, and 4-(2-hydroxyethoxy)phenyl-(2-hydroxy-2-methylpropyl) ketone (sold by Ciba Speciality Chemicals as IRGACURE® 2959); and Oligo [2-hydroxy-2-methyl-1-[4-(1-methylvinyl) phenyl]propanone] (sold by Lambeth spa, Gallarate, Italy as ESACURE® KIP EM.

The dispersed aqueous phase of a HIPE may have water, and may also have one or more components, such as initiator, photoinitiator, or electrolyte, wherein in certain embodiments, the one or more components are at least partially water soluble.

One component of the aqueous phase may be a water-soluble electrolyte. The water phase may contain from about 0.2% to about 40%, in certain embodiments from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte may include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator may be present at up to about 20 mole percent based on the total moles of polymerizable monomers present in the oil phase. The initiator may be present in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine)dihydrochloride, and other suitable azo initiators. To reduce the potential for premature polymerization which may clog the emulsification system, addition of the initiator to the monomer phase may be just after or near the end of emulsification.

Photoinitiators present in the aqueous phase may be at least partially water soluble and may have between about 0.05% and about 10%, and in certain embodiments between about 0.2% and about 10% by weight of the aqueous phase. Lower amounts of photoinitiator allow light to better penetrate the HIPE foam, which may provide for polymerization deeper into the HIPE foam. However, if polymerization is done in an oxygen-containing environment, there should be enough photoinitiator to initiate the polymerization and overcome oxygen inhibition. Photoinitiators may respond rapidly and efficiently to a light source with the production of radicals, cations, and other species that are capable of initiating a polymerization reaction. The photoinitiators used in the present invention may absorb UV light at wavelengths of from about 200 nanometers (nm) to about 800 nm, in certain embodiments from about 200 nm to about 350 nm, and in certain embodiments from about 350 nm to about 450 nm. If the photoinitiator is in the aqueous phase, suitable types of water-soluble photoinitiators include benzophenones, benzils, and thioxanthones. Examples of photoinitiators include 2,2'-Azobis[2-(2-imidazolin-2-yl)propane]dihydrochloride; 2,2'-Azobis[2-(2-imidazolin-2-yl)propane]disulfate dehydrate; 2,2'-Azobis(1-imino-1-pyrrolidino-2-ethylpropane)dihydrochloride; 2,2'-Azobis[2-methyl-N-(2-hydroxyethyl)propionamide]; 2,2'-Azobis(2-methylpropionamidine)dihydrochloride; 2,2'-dicarboxymethoxydi- benzalacetone, 4,4'-dicarboxymethoxydibenzalacetone, 4,4'-dicarboxymethoxydibenzalcyclohexanone, 4-dimethylamino-4'-carboxymethoxydibenzalacetone; and 4,4'-disulphoxymethoxydibenzalacetone. Other suitable photoinitiators that may be used in the present invention are listed in U.S. Pat. No. 4,824,765 (Sperry et al.) issued Apr. 25, 1989.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler pieces, for example starch, titanium dioxide, carbon black, or calcium carbonate; fibers; chain transfer agents; odor absorbers, for example activated carbon particulates; dissolved polymers; dissolved oligomers; and the like.

The heterogeneous mass comprises enrobeable elements and discrete pieces of foam. The enrobeable elements may be a web such as, for example, nonwoven, a fibrous structure, an air-laid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof.

The enrobeable elements may be, for example, conventional absorbent materials such as creped cellulose wadding, fluffed cellulose fibers, wood pulp fibers also known as airfelt, and textile fibers. The enrobeable elements may also be fibers such as, for example, synthetic fibers, thermoplastic particulates or fibers, tricomponent fibers, and bicomponent fibers such as, for example, sheath/core fibers having the following polymer combinations: polyethylene/polypropylene, polyethylvinyl acetate/polypropylene, polyethylene/polyester, polypropylene/polyester, copolyester/polyester, and the like. The enrobeable elements may be any combination of the materials listed above and/or a plurality of the materials listed above, alone or in combination.

The enrobeable elements may be hydrophobic or hydrophilic. The enrobeable elements may be treated to be made hydrophobic. The enrobeable elements may be treated to become hydrophilic.

The constituent fibers of the heterogeneous mass may be comprised of polymers such as polyethylene, polypropylene, polyester, and blends thereof. The fibers may be spunbound fibers. The fibers may be meltblown fibers. The fibers may comprise cellulose, rayon, cotton, or other natural materials or blends of polymer and natural materials. The fibers may also comprise a super absorbent material such as polyacrylate or any combination of suitable materials. The fibers may be monocomponent, bicomponent, and/or biconstituent, non-round (e.g., capillary channel fibers), and may have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e. capillary and round) and the like. The constituent fibers may range from about 0.1 denier to about 100 denier.

In one aspect, known absorbent web materials in an as-made may be considered as being homogeneous throughout. Being homogeneous, the fluid handling properties of the absorbent web material are not location dependent, but are substantially uniform at any area of the web. Homogeneity may be characterized by density, basis weight, for example, such that the density or basis weight of any particular part of the web is substantially the same as an average density or basis weight for the web. By the apparatus and method of the present invention, homogeneous fibrous absorbent web materials are modified such that they are no longer homogeneous, but are heterogeneous, such that the fluid handling properties of the web material are location dependent. Therefore, for the heterogeneous absorbent materials of the present invention, at discrete locations the density or basis weight of the web may be substantially different than the average density or basis weight for the web. The heterogeneous nature of the absorbent web of the present invention permits the negative aspects of either of permeability or capillarity to be minimized by rendering discrete portions highly permeable and other discrete portions to have high capillarity. Likewise, the tradeoff between permeability and capillarity is managed such that delivering relatively higher permeability may be accomplished without a decrease in capillarity.

The heterogeneous mass may also include superabsorbent material that imbibe fluids and form hydrogels. These materials are typically capable of absorbing large quantities of body fluids and retaining them under moderate pressures. The heterogeneous mass may include such materials dispersed in a suitable carrier such as cellulose fibers in the form of fluff or stiffened fibers.

The heterogeneous mass may include thermoplastic particulates or fibers. The materials, and in particular thermoplastic fibers, may be made from a variety of thermoplastic polymers including polyolefins such as polyethylene (e.g., PULPEX®) and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, and the like. The surface of the hydrophobic thermoplastic fiber may be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants may also be used. These surfactants may be applied to the thermoplastic fibers at levels of, for example, from about 0.2 to about 1 g. per sq. of centimeter of thermoplastic fiber.

Suitable thermoplastic fibers may be made from a single polymer (monocomponent fibers), or may be made from more than one polymer (e.g., bicomponent fibers). The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention may include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers may be concentric or eccentric. As used herein, the terms "concentric" and "eccentric" refer to whether the sheath has a thickness that is even, or uneven, through the cross-sectional area of the bicomponent fiber. Eccentric bicomponent fibers may be desirable in providing more compressive strength at lower fiber thicknesses. Suitable bicomponent fibers for use herein may be either uncrimped (i.e. unbent) or crimped (i.e. bent). Bicomponent fibers may be crimped by typical textile means such as, for example, a stuffer box method or the gear crimp method to achieve a predominantly two-dimensional or "flat" crimp.

The length of bicomponent fibers may vary depending upon the particular properties desired for the fibers and the web formation process. Typically, in an airlaid web, these thermoplastic fibers have a length from about 2 mm to about 12 mm long such as, for example, from about 2.5 mm to about 7.5 mm long, and from about 3.0 mm to about 6.0 mm long. Nonwoven fibers may be between 5 mm long and 75 mm long, such as, for example, 10 mm long, 15 mm long, 20 mm long, 25 mm long, 30 mm long, 35 mm long, 40 mm long, 45 mm long, 50 mm long, 55 mm long, 60 mm long, 65 mm long, or 70 mm long. The properties-of these thermoplastic fibers may also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine may have a decitex in the range of about 1.0 to about 20 such as, for example, from about 1.4 to about 10, and from about 1.7 to about 7 decitex.

The compressive modulus of these thermoplastic materials, and especially that of the thermoplastic fibers, may also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers may be used to alter the properties, and especially the density characteristics, of the respective thermally bonded fibrous matrix.

The heterogeneous mass may also include synthetic fibers that typically do not function as binder fibers but alter the mechanical properties of the fibrous webs. Synthetic fibers include cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. These might include, for example, polyester fibers such as polyethylene terephthalate (e.g., DACRON® and KODEL®), high melting crimped polyester fibers (e.g., KODEL® 431 made by Eastman Chemical Co.) hydrophilic nylon (HYDROFIL®), and the like. Suitable fibers may also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length may vary depending upon the particular properties desired for these fibers. Typically they have a length from about 0.3 to 7.5 cm, such as, for example from about 0.9 to about 1.5 cm. Suitable nonbonding thermoplastic fibers may have a decitex in the range of about 1.5 to about 35 decitex, such as, for example, from about 14 to about 20 decitex.

However structured, the total absorbent capacity of the heterogeneous mass containing foam pieces should be compatible with the design loading and the intended use of the mass. For example, when used in an absorbent article, the size and absorbent capacity of the heterogeneous mass may be varied to accommodate different uses such as incontinence pads, pantiliners, regular sanitary napkins, or overnight sanitary napkins. The heterogeneous mass may also include other optional components sometimes used in absorbent webs. For example, a reinforcing scrim may be positioned within the respective layers, or between the respective layers, of the heterogeneous mass.

The heterogeneous mass comprising open-cell foam pieces produced from the present invention may be used as an absorbent core or a portion of an absorbent core in absorbent articles, such as feminine hygiene articles, for example pads, pantiliners, and tampons; disposable diapers; incontinence articles, for example pads, adult diapers; home-care articles, for example wipes, pads, towels; and beauty care articles, for example pads, wipes, and skin care articles, such as used for pore cleaning.

The heterogeneous mass may be used as an absorbent core for an absorbent article. The absorbent core may be relatively thin, less than about 5 mm in thickness, or less than about 3 mm, or less than about 1 mm in thickness. Cores having a thickness of greater than 5 mm are also contemplated herein. Thickness may be determined by measuring the thickness at the midpoint along the longitudinal centerline of the absorbent structure by any means known in the art for doing while under a uniform pressure of 0.25 psi. The absorbent core may comprise absorbent gelling materials (AGM), including AGM fibers, as is known in the art.

The heterogeneous mass may be formed or cut to a shape, the outer edges of which define a periphery. Additionally, the heterogeneous mass may be continuous such that it may be rolled or wound upon itself, with or without the inclusion of preformed cut lines demarcating the heterogeneous mass into preformed sections.

When used as an absorbent core, the shape of the heterogeneous mass may be generally rectangular, circular, oval, elliptical, or the like. Absorbent core may be generally centered with respect to the longitudinal centerline and transverse centerline of an absorbent article. The profile of absorbent core may be such that more absorbent is disposed near the center of the absorbent article. For example, the absorbent core may be thicker in the middle, and tapered at the edges in a variety of ways known in the art.

Without being bound by theory, it has been found that it is possible to generate single layer absorbent structures that exhibit behavior that breaks the trade-off traditionally found between permeability and capillary suction. This trade-off may be effectively represented by plotting all materials in a chart where the abscissa represents permeability or an equivalent measure of the inverse resistance to flow in the porous media (i.e. conductivity) and the ordinate represents Capillary Work Potential or an equivalent metric for capillary suction (i.e. Capillary Pressure at 50% saturation). It is worthwhile noting that if the metric chosen to represent capillary suction is an extensive metric such as the Capillary Work Potential, then a limitation on the validity of such metric for a caliper range must be specified. Within this chart exemplified by FIG. 20 two domains may be identified where the ideal structure represented by bundle of capillary tubes is the chosen division line. The division line 88 represents the ideal case of a bunch of parallel capillary tubes. The division line 88 represents the trade-off ($CWP_{t\text{-}o}$) boundary. The continuous division line 88 may be misinterpreted to represent a theoretical maximum for all existing porous media.

The trade-off curve (which becomes a straight line when the plot is converted into a log-log plot) may be mathematically described by mean of the following equation:

$$CWP = \frac{1}{2} \frac{(\varepsilon \gamma \cos\alpha)^2}{\rho g k} \qquad \text{Eq. (1)}$$

Where $\varepsilon$ is the material porosity or degree of void, $\kappa$ is the porous material permeability, $\gamma$ is the surface tension of the fluid absorbed, $\rho$ is fluid density, $\alpha$ is the contact angle of the fluid and the PM and g is the gravitational constant, 9.81 m/s$^2$.

Where CWP stands for Capillary Work Potential and is defined as the integral of the capillary pressure curve as function of saturation level for the whole range of saturations from fully dry (S=0) to fully wet (S=1) or in mathematical terms:

$$CWP \stackrel{def}{=} \frac{1}{A} \int_{S=0}^{S=1} P dV \qquad \text{Eq. (2)}$$

Specifically, The theoretical trade-off curve can be derived from an ideal model structure, i.e. bundle of parallel capillary tube of same diameter, using the same fluid properties used to measure empirically CWP in the lab (given surface tension and contact angle). The CWP is an extensive property (i.e. its value depends on the amount of material) and it is therefore linked to the caliper of the material sample used to run the test. We have found useful to describe capillary suction by means of Capillary Work Potential for the materials typically used in the current industry standard for absorbent articles of less than 15 mm in caliper. Starting from a single tube, neglecting the impact of gravitational field on capillary action, the driving force for capillary suction is the capillary pressure given by Young-Laplace Equation:

$$P = \frac{2\gamma \cos\alpha}{R} \qquad \text{Eq. (3)}$$

We recognize that parallel and non-interconnect capillary tubes will have the same capillary pressure, since each tube does not impact the formation of the meniscus of an adjacent tube (i.e. if one places a number N of tubes of same radius inside a reservoir they will all reach the same height, regardless of the number).

This will be used to estimate the Capillary Work Potential (CWP), of the structure, defined by the Integral of the Capillary Pressure over the volume of acquired fluid going from an empty capillary to a fully saturated one, as described by eq. (4) below:

$$CWP = \frac{1}{A} \int_{S=0}^{S=1} P dV \qquad \text{Eq. (4)}$$

As the work per unit area (expressed in mJ/m$^2$) that the bundle of tubes will exert on the fluid to move it. To link CWP with Permeability, we need an expression linking geometry (radius) with permeability.

We know that the Permeability of the single capillary tube can be derived from the Darcy's Law (5) combined with Haegen-Poiseuille Equation:

$$Q = \frac{kA}{\mu} \frac{P}{h} \qquad \text{Eq. (5)}$$

$$Q = \frac{\pi R^4}{8\mu} \frac{P}{h} \qquad \text{Eq. (6)}$$

Which, ultimately gives:

$$k = \frac{R^2}{8} \qquad \text{Eq. (7)}$$

Conventionally, Eq. (7) has been used to define a Darcy Number as the ratio between k and R$^2$. With similar arguments, for a bundle of capillary tubes, it has been shown that[1]:

$$k = \varepsilon \frac{R^2}{8} \qquad \text{Eq. (8)}$$

Where $\varepsilon$ is the porosity of the resulting structure, which is linked to the Number of capillary tubes in the bundle and the volume of the sample.

[1] H. K. Dahle, M. A. Celia, S. M. Hassanizadeh, Transport Porous Med. 2005, 58:5-22

Recalling now Eq. (4), we have:

$$CWP = \frac{1}{A}\int_{S=0}^{S=1}\left(\frac{2\gamma\cos\alpha}{R}\right)dV = \int_{S=0}^{S=1}\left(\frac{2\gamma\cos\alpha}{R}\right)\varepsilon\, dh \qquad \text{Eq. (9)}$$

Where we have made use of the expression:

$$V = Ah\varepsilon \qquad \text{Eq. (10)}$$

Linking the volume of the fluid with the physical volume of the capillary bundle by mean of the porosity of the system.

Since saturation is simply defined as the ratio of the volume occupied by the fluid over the total void volume, or equivalently the ratio between the height of the fluid level vs. the total system height:

$$S = \frac{V}{V_0} = \frac{A\varepsilon h}{A\varepsilon h_0} = \frac{h}{h_0} \qquad \text{Eq. (11)}$$

Where h is the height of the fluid level and goes from 0, when S=0, to $h_0$, when S=1.

The integral in Eq. (9) can then be rewritten as integral of the height of the liquid level as:

$$CWP = \int_{h=0}^{h=h_0}\left(\frac{2\gamma\cos\alpha}{R}\right)\varepsilon\, dh = \left(\frac{2\gamma\cos\alpha}{R}\right)\varepsilon h_0 \qquad \text{Eq. (12)}$$

Where the length of the tubes, h0, shows up as contribution (accounting for capacity).

This quantity can be easily estimated from other known quantities using the equilibrium condition at a given pressure for each capillary tube:

$$h_0 = \frac{2\gamma\cos\alpha}{R\rho g} \qquad \text{Eq. (13)}$$

Combining Eq. (12) and (13) we obtain:

$$CWP = \left(\frac{2\gamma\cos\alpha}{R}\right)^2\frac{\varepsilon}{\rho g} \qquad \text{Eq. (14)}$$

Where ρ is the density of the fluid and g is the gravitational constant 9.81 m/s².

Substituting Eq. (8) into Eq. (14) yields the final form of the sought theoretical relationship for the trade-off between Capillary Suction, in the form of Capillary Work Potential, and Permeability:

$$\boxed{CWP = \frac{1}{2}\frac{(\varepsilon\gamma\cos\alpha)^2}{\rho g k}} \qquad \text{Eq. (15)}$$

As Eq. (15) shows, this trade-off is clearly fluid-dependent via density, ρ, surface tension, γ, and contact angle, α. For the purpose of setting a theoretical limit, we have considered in the calculations the case of porosity ε=1, corresponding to 100% porous media, with fluid having perfect wettability ($\cos(\alpha)=1$) and high surface tension of 0.072 N/m (water) and density of 1 g/cm³ (water).

The trade-off line divides the domain into two regions:

$$CWP < CWP_{t-o} = \frac{1}{2}\frac{(\varepsilon\gamma\cos\alpha)^2}{\rho g k} \qquad \text{Eq. (16)-a}$$

And $$CWP > CWP_{t-o} \qquad \text{Eq. (16)-b}$$

Applicants have found a method to systematically cross the trade-off boundary for a single layer system, left-to-right, creating structures that show:

$$CWP > CWP_{t-o} \qquad \text{Eq. (17)}$$

This has been achieved by a two-step process:

By integrating a high capillary suction PM into a high permeability substrate, and by providing a continuous Transition Zone (TZ) between the two materials, we obtain a heterogeneous structure that because of its nature will naturally sit on the trade-off curve in the region of very low permeabilities (behavior dominated by the highest resistance to flow material) and high capillary suction.

Formation means known for opening a generally planar fibrous web may be utilized in the present invention to modify as-made absorbent materials into absorbent materials residing beyond the traditional capillarity permeability tradeoff boundary. Formation means may comprise a pair of inter-meshing rolls, typically steel rolls having inter-engaging ridges or teeth and grooves. However, it is contemplated that other means for achieving formation can be utilized, such as the deforming roller and cord arrangement disclosed in US 2005/0140057 published Jun. 30, 2005. Therefore, all disclosure of a pair of rolls herein is considered equivalent to a roll and cord, and a claimed arrangement reciting two inter-meshing rolls is considered equivalent to an inter-meshing roll and cord where a cord functions as the ridges of a mating inter-engaging roll. In one embodiment, the pair of intermeshing rolls of the instant invention can be considered as equivalent to a roll and an inter-meshing element, wherein the inter-meshing element can be another roll, a cord, a plurality of cords, a belt, a pliable web, or straps. Likewise, other known formation technologies, such as creping, necking/consolidation, corrugating, embossing, button break, hot pin punching, knife or laser cutting and the like are believed to be able to produce absorbent materials having a higher some degree of relatively higher permeability without a meaningful decrease in capillary pressure. Formation means utilizing rolls include "ring rolling", a "SELF" or "SELF'ing" process, in which SELF stands for Structural Elastic Like Film, as "micro-SELF", and "rotary knife aperturing" (RKA); as described in U.S. Pat. No. 7,935,207 Zhao et al., granted May 3, 2011.

During the opening and expansion process, the width of the material grows as a consequence. In addition, three phenomena take place. The first is an increase in permeability as a function of spacing. The increase in permeability as a function of spacing may be driven by the formation of cracks and fractures in the heterogeneous structure, with permeability of the laminate approaching the permeability of the carrier. The second is a reduction in density for the high capillary suction material as function of spreading (being spread across a wider length), which results in a net decrease in the CWP. The third is an increase in the intrinsic capillary suction as function of perimeter lines, driven by increase in the surface to volume ratio. The increase in surface to volume ratio is because of the creation of new surfaces and the decrease in material basis weight. Without being bound by theory, it is important to control the extent of the opening and expansion process so as not to produce an opening that behaves like a hole or aperture. Each liquid can be defined by its surface tension and its viscosity. Liquid surface tension and liquid viscosity (or the liquid density) can be used to define a liquid capillarity length. For example human arterial blood it is estimated that the capillarity length is at about 54 microns, whereas a 0.9% saline solution is even longer. It has been found that the mechanical openings need to be restricted to about five (5) times the capillarity length of the specific liquid being absorbed to sustain a point above and beyond the capillarity permeability tradeoff curve. So for the example of human arterial blood the physical separation between the mechanically openings, within the heterogeneous structure, would need to be less than about 250 microns (ca 5 times the capillarity length). If the physical separation of the opening is greater than about ca 5 times the capillarity length the material will no longer reside above the capillarity-permeability tradeoff boundary and will fall back within the traditional capillarity permeability tradeoff regime.

Because of the nature of these changes, it is possible to increase the permeability of any heterogeneous structure, provided that the carrier material and the absorbent core have distinct permeabilities, while keeping the CWP virtually constant, by means of increased perimeter lines (perimeter of the cracks, within the capillarity length requirements detailed above) for any spacing below a factor equal to the increase in CWP driven by perimeter line.

Therefore, the invention allows making absorbent structures with the ability to achieve capillarity pressure (measured as CWP in mJ/m$^2$) at a level greater than ideal behavior (trade-off curve) at permeability levels between 100 and 10,000 (measured in darcys).

Therefore, the invention allows making absorbent structures with the ability to achieve capillarity pressure (measured as CWP in mJ/m$^2$) at a level greater than ideal behavior (trade-off curve) at permeability levels between 100 and 10,000 (measured in darcys).

For sake of clarity, a medium with a permeability of 1 Darcy permits a flow of 1 cm$^3$/s of a fluid with viscosity 1 cP (1 mPa·s) under a pressure gradient of 1 atm/cm acting across an area of 1 cm$^2$.

As shown in the table below, the additional surface area and high capillarity allows breaking the traditional tradeoff between capillarity and permeability. As shown in the table below, with the exception of Sample A, all other Prior Art samples are on or below the ideal behavior equation.

| Material | BW (gsm) | k (darcys) | CWP (mJ/m$^2$) |
|---|---|---|---|
| 60 gsm AQL + HIPE Foam 2 full | 170 | 13 | 5032 |
| Sample A | 119 | 316 | 4573 |
| Infinity Topsheet(TS) | 14 | 443 | 96 |
| 14 gsm Philic Bico | 14 | 286 | 88 |
| 28 gsm Philic Bico | 28 | 129 | 129 |
| 77 gsm secondary topsheet(STS) | 77 | 639 | 382 |
| 24 gsm Yanjan Topsheet | 24 | 1021 | 109 |
| 30 gsm SL | 30 | 645 | 292 |
| 50 gsm SL | 50 | 999 | 234 |
| 43 gsm AQL | 43 | 1547 | 115 |
| 60 gsm AQL | 60 | 2112 | 144 |
| 180 gsm - G2 Core | 180 | 748 | 415 |
| HIPE Foam 1 | 86 | 368 | 1101 |
| HIPE Foam 2 | 110 | 8 | 5754 |
| HIPE foam 3 | 196 | 13 | 3063 |

Figure 20:
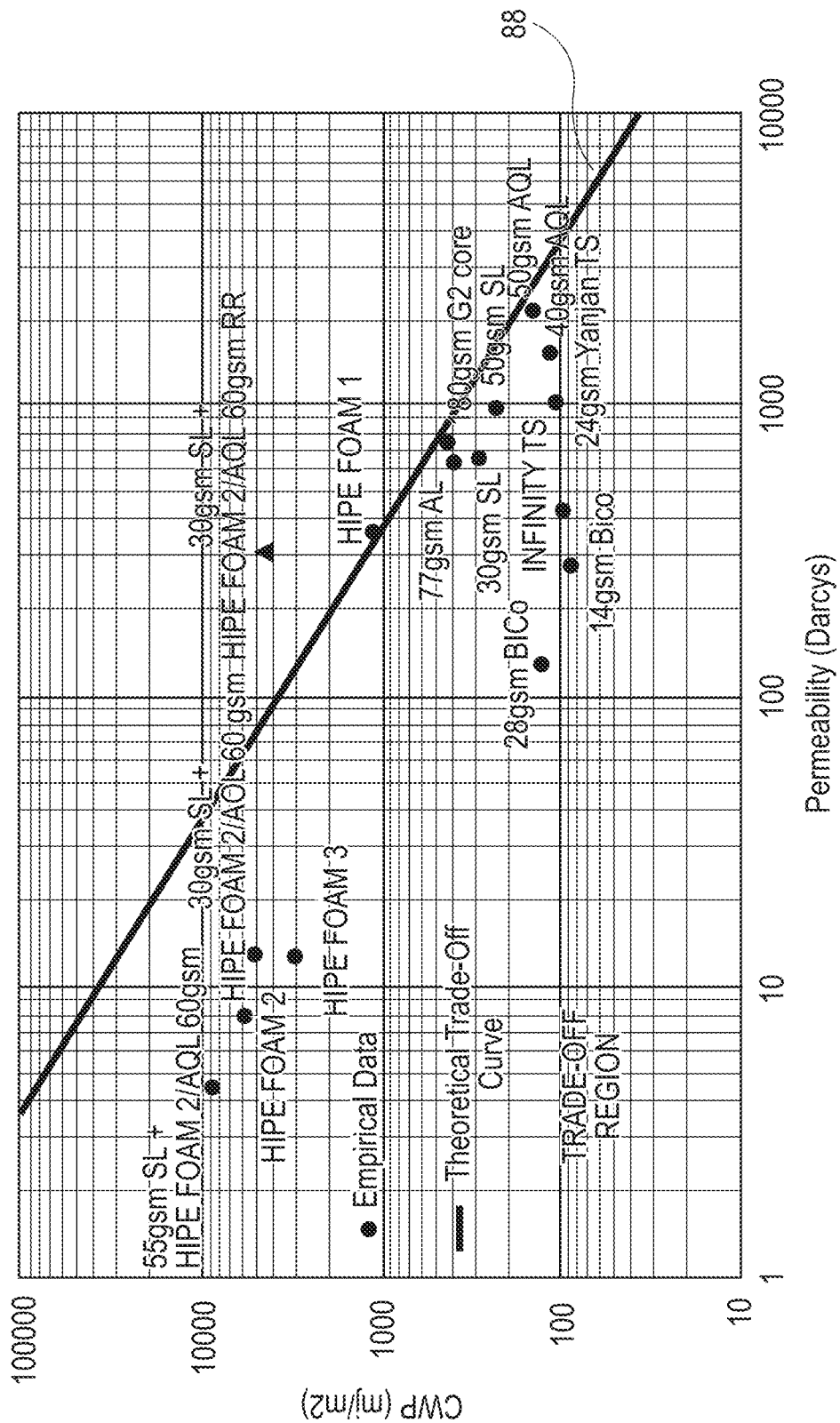
FIG. 20 is a graph with Capillary Work Potential along the Y axis and Permeability along the X axis.

The samples above represent various topsheets (TS), secondary topsheets (STS), spunlace materials (SL), aquistion layer (AQL), bico fibers, superabsorbent cores, and foam layers. The data table is best exemplified when shown as a graph as viewed in FIG. 20. As shown in FIG. 20, all the Prior Art samples are on or below the ideal behavior line. In contrast, due to the novel properties of the absorbent structure single stratum, the absorbent structure single stratum sample is above the theoretical trade-off line. The absorbent structure single stratum exhibits a Capillarity Work Potential greater than the Capillarity Work Potential trade-off Boundary. The absorbent structure single stratum exhibits permeability greater than the Capillarity Work Potential trade-off Boundary for a given Capillary Work Potential.

The absorbent structure single stratum may exhibit a Capillarity Work Potential of between 100 mJ/m$^2$ and 10,000 mJ/m$^2$ and a permeability between 10 Darcy and 10,000 Darcy provided that the Capillary Work Potential is greater than the Capillarity Work Potential trade-off Boundary. The absorbent structure single stratum may exhibit a Capillarity Work Potential of between 1,000 mJ/m$^2$ and 10,000 mJ/m$^2$ and a permeability between 10 Darcy and 10,000 Darcy provided that the Capillary Work Potential is greater than the Capillarity Work Potential trade-off Boundary. The absorbent structure single stratum may exhibit a Capillary Work Potential of between 1,000 mJ/m$^2$ and 10,000 mJ/m$^2$ and a permeability between 10 Darcy and 1,000 Darcy provided that the Capillary Work Potential is greater than the Capillarity Work Potential trade-off Boundary.

The absorbent structure single stratum may exhibit a Capillarity Work Potential for a fixed permeability that is greater than the Capillarity Work Potential trade-off Boundary and less than 20 times the Capillarity Work Potential trade-off and a permeability greater than the Capillarity Work Potential trade-off Boundary for a given Capillary Work Potential.

The absorbent structure single stratum may serve as any portion of an absorbent article. The absorbent structure single stratum may serve as the absorbent core of an absorbent article. The absorbent structure single stratum may serve as a portion of the absorbent core of an absorbent article. More than one absorbent structure single stratum may be combined wherein each absorbent structure single stratum differs from at least one other absorbent structure single stratum in either the choice of enrobeable elements or by a characteristic of its open-cell foam pieces. The different two or more absorbent structures single stratums may be combined to form an absorbent core. The absorbent article may further comprise a topsheet and a backsheet.

The absorbent structure single stratum may be used as a topsheet for an absorbent article. The absorbent structure single stratum may be combined with an absorbent core or may only be combined with a backsheet.

The absorbent structure single stratum may be combined with any other type of absorbent layer such as, for example, a storage or acquisition layer comprising a layer of cellulose, a layer comprising superabsorbent gelling materials, a layer of absorbent airlaid fibers, or a layer of absorbent foam. Other absorbent layers not listed are contemplated herein.

The absorbent structure single stratum may be utilized by itself for the absorption of fluids without placing it into an absorbent article.

An absorbent article may comprise a liquid pervious topsheet. The topsheet suitable for use herein may comprise wovens, non-wovens, and/or three-dimensional webs of a liquid impermeable polymeric film comprising liquid permeable apertures. The topsheet for use herein may be a single layer or may have a multiplicity of layers. For example, the wearer-facing and contacting surface may be provided by a film material having apertures which are provided to facilitate liquid transport from the wearer facing surface towards the absorbent structure. Such liquid permeable, apertured films are well known in the art. They provide a resilient three-dimensional fibre-like structure. Such films have been disclosed in detail for example in U.S. Pat. Nos. 3,929,135, 4,151,240, 4,319,868, 4,324,426, 4,343,314, 4,591,523, 4,609,518, 4,629,643, 4,695,422 or WO 96/00548.

The absorbent articles of FIGS. 1 to 11 comprising embodiments of the absorbent structure may also comprise a backsheet and a topsheet. The backsheet may be used to prevent the fluids absorbed and contained in the absorbent structure from wetting materials that contact the absorbent article such as underpants, pants, pyjamas, undergarments, and shirts or jackets, thereby acting as a barrier to fluid transport. The backsheet may also allow the transfer of at least water vapour, or both water vapour and air through it.

Especially when the absorbent article finds utility as a sanitary napkin or panty liner, the absorbent article may be also provided with a panty fastening means, which provides means to attach the article to an undergarment, for example a panty fastening adhesive on the garment facing surface of the backsheet. Wings or side flaps meant to fold around the crotch edge of an undergarment may be also provided on the side edges of the napkin.

FIG. 1 is a plan view of a sanitary napkin 10 comprising a topsheet 12, a backsheet (not shown), an absorbent core 16 located between the topsheet 12 and the backsheet, a longitudinal axis 24, and a transverse axis 26. The absorbent core 16 comprises of a heterogeneous mass 18 comprising elements 30 and one or more discrete foam pieces 20 that enrobe the at least one element 30 of the heterogeneous mass 18. As shown in FIG. 1 the elements 30 are fibers 22. A portion of the topsheet is cut out in order to show underlying portions.

Figure 2:
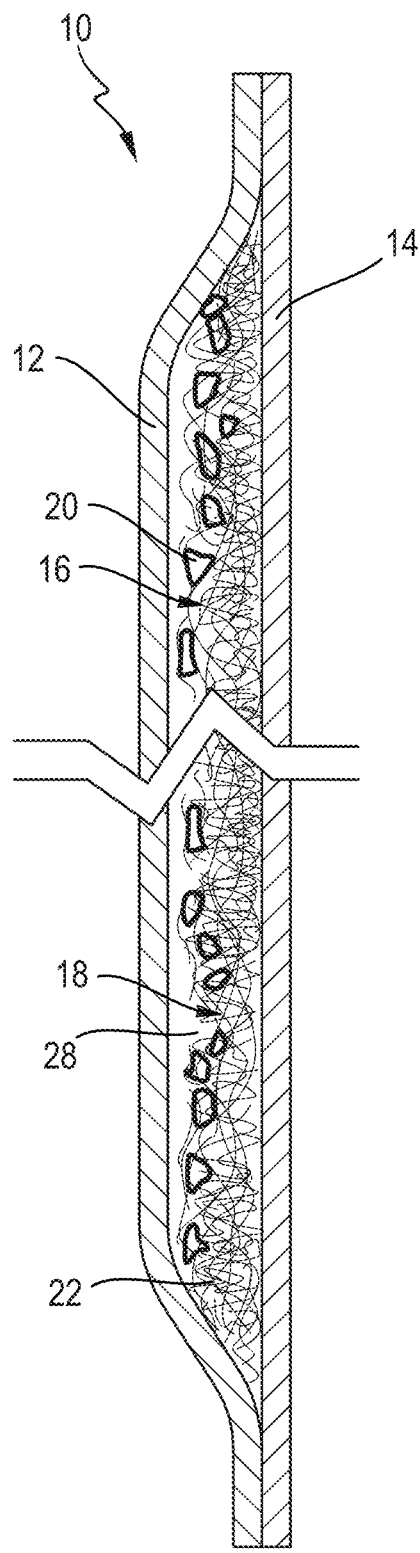
FIG. 2 is a cross section view of the absorbent article of FIG. 1 taken along line 2-2.
Figure 3:
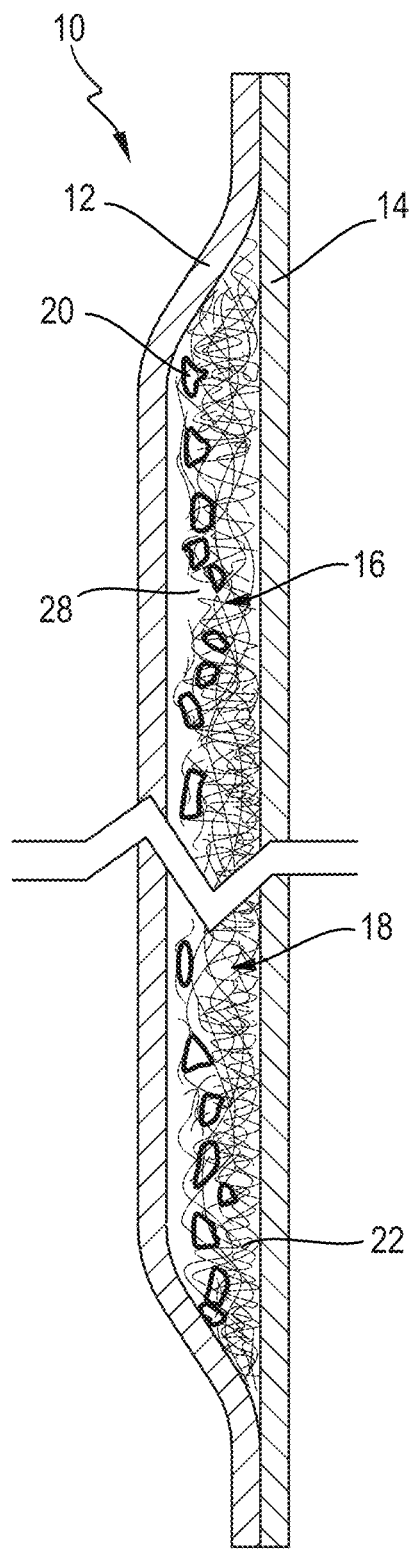
FIG. 3 is a cross section view of the absorbent article of FIG. 1 taken along line 3-3.

FIGS. 2 and 3 are cross sections of pad shown in FIG. 1, cut through the 2-2 vertical plane along the longitudinal axis 24 and cut through the 3-3 vertical plane along the transverse axis 26, respectively. As may be seen in FIGS. 2 and 3, the absorbent core 16 is between the topsheet 12 and the backsheet 14. As shown in the embodiment of FIGS. 2 and 3, the discrete foam pieces 20 are spread out throughout the absorbent core and enrobe the elements 30 of the heterogeneous mass 18. The discrete pieces 20 of foam may extend beyond the enrobeable elements to form part of the outer surface of the heterogeneous mass. Additionally, discrete pieces of foam may be fully intertwined within the heterogeneous mass of the absorbent core. Voids 28 containing gas are located between the fibers 22.

Figure 4:
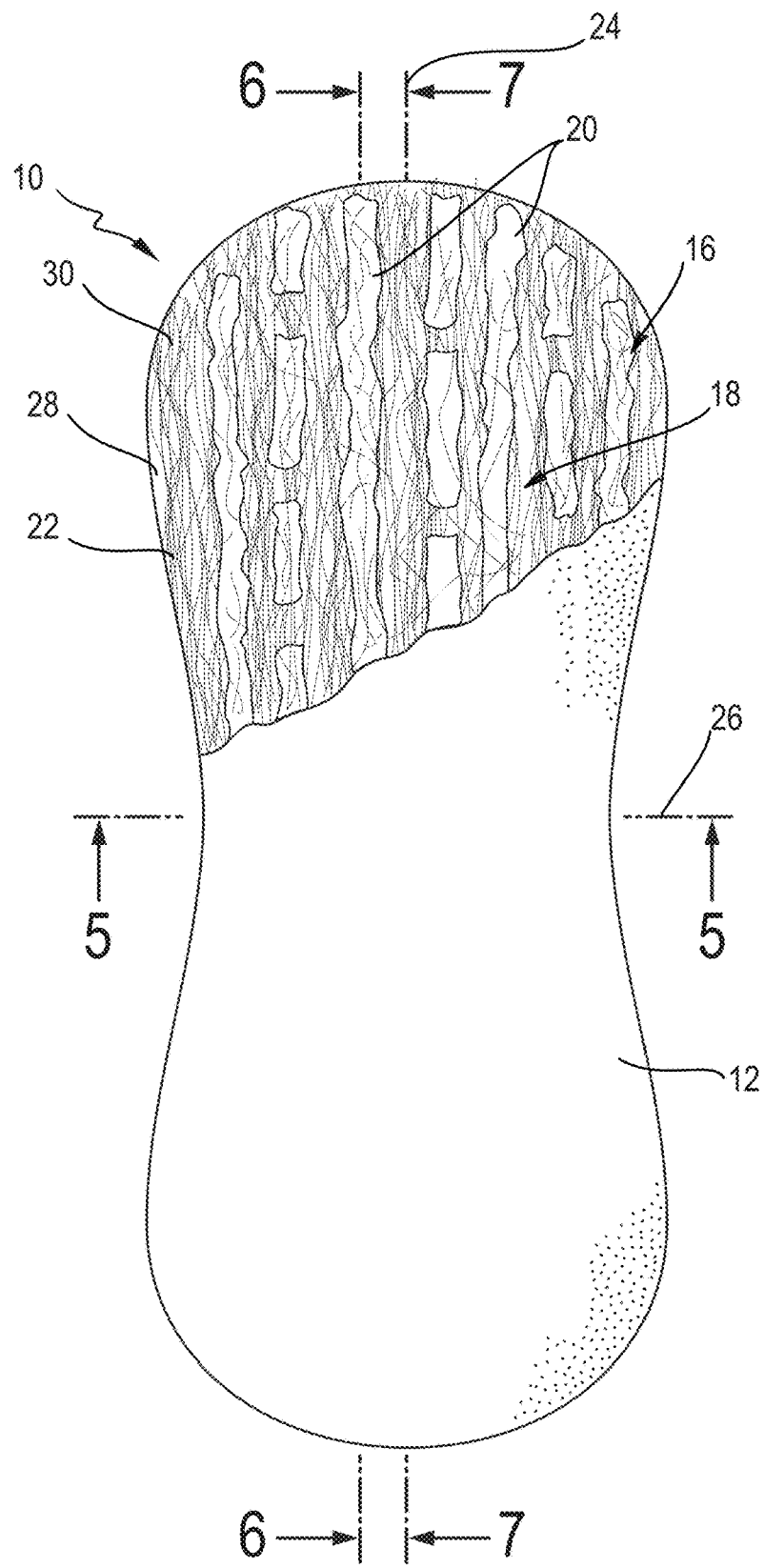
FIG. 4 is a top view of an absorbent article.

FIG. 4 is a plan view of a sanitary napkin 10 illustrating an embodiment of the invention. The sanitary napkin 10 comprises a topsheet 12, a backsheet (not shown), an absorbent core 16 located between the topsheet 12 and the backsheet, a longitudinal axis 24, and a transverse axis 26. The absorbent core 16 comprises of a heterogeneous mass 18 comprising elements 30 and one or more discrete foam pieces 20 that enrobe the at least one element 30 of the heterogeneous mass 18. As shown in FIG. 4, the elements 30 are fibers 22. A portion of the topsheet is cut out in order to show underlying portions. As shown in FIG. 4 the discrete foam pieces 20 may be continuous along an axis of the heterogeneous mass, such as, for example, the longitudinal axis. Further, the discrete foam 20 may be arranged to form a line in the heterogeneous mass. The discrete foam pieces 20 are shown proximate to the top of the heterogeneous mass 18 but may also be located at any vertical height of the heterogeneous mass 18 such that enrobeable elements 30 may be located above and below the one or more of the discrete foam pieces 20.

Figure 5:
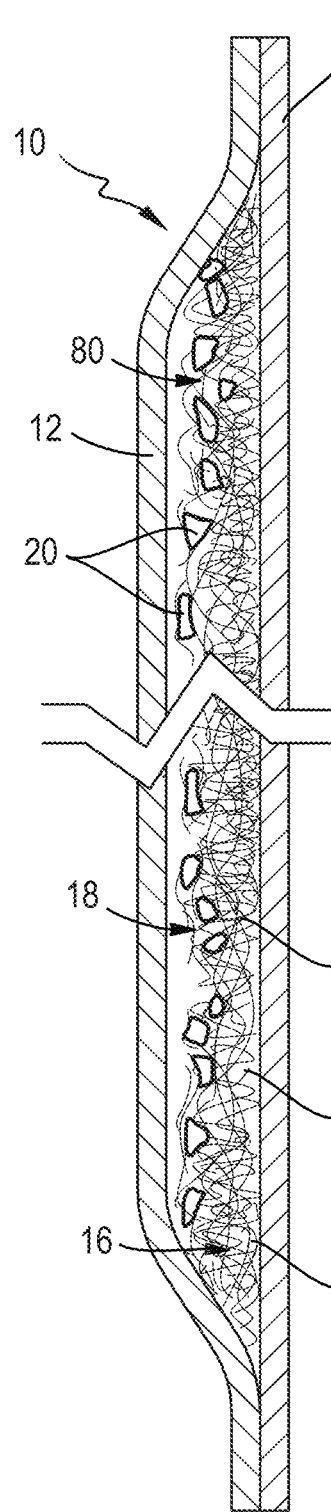
FIG. 5 is a cross section view of the absorbent article of FIG. 4 taken along line 5-5.
Figure 6:
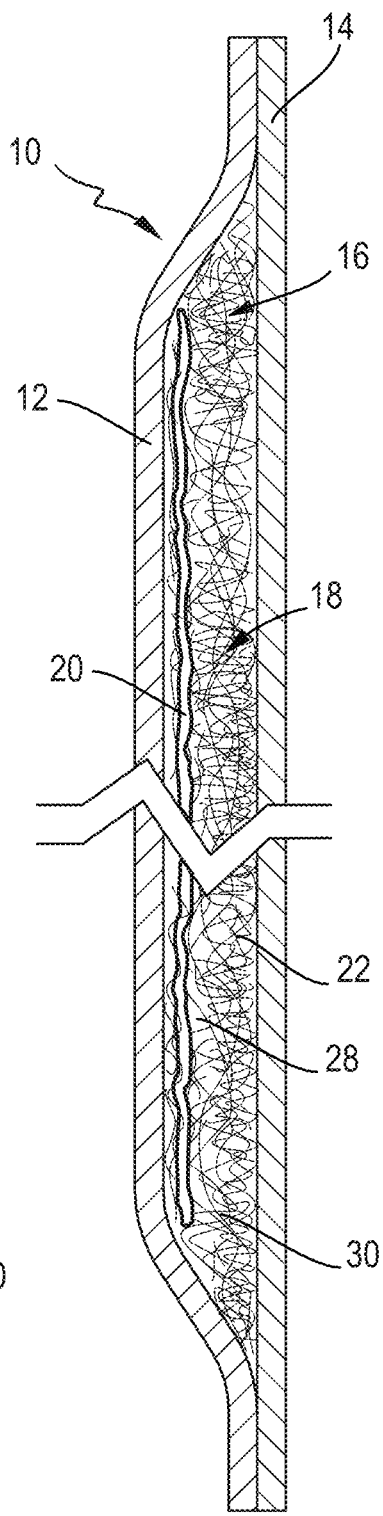
FIG. 6 is a cross section view of the absorbent article of FIG. 4 taken along line 6-6.
Figure 7:
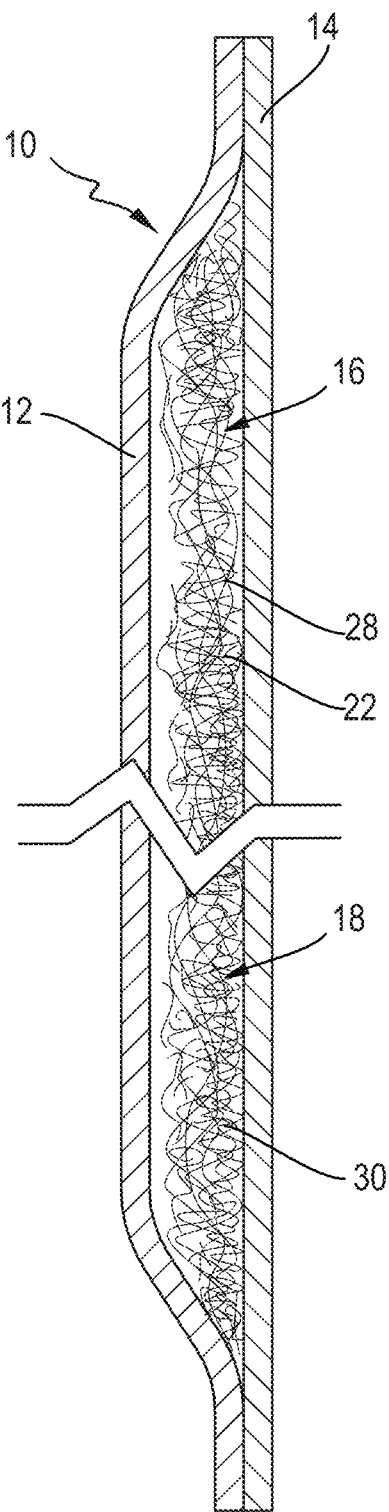
FIG. 7 is a cross section view of the absorbent article of FIG. 4 taken along line 7-7.

FIGS. 5, 6 and 7 are cross sections of the pad shown in FIG. 4, cut through the 5-5, the 6-6, and the 7-7 vertical planes, respectively. The 5-5 vertical plane is parallel to the transverse axis of the pad and the 6-6 and 7-7 vertical planes are parallel to the longitudinal axis. As may be seen in FIGS. 5 to 7, the absorbent core 16 is between the topsheet 12 and the backsheet 14. As shown in the embodiment of FIG. 5, the discrete foam pieces 20 are spread out throughout the absorbent core and enrobe the elements 30 of the heterogeneous mass 18. As shown in FIG. 6, a discrete foam piece 20 may be continuous and extend along the heterogeneous mass. As shown in FIG. 7, the heterogeneous mass may not have any discrete foam pieces along a line cross section of the absorbent core. Voids 28 containing gas are located between the fibers 22.

Figure 8:
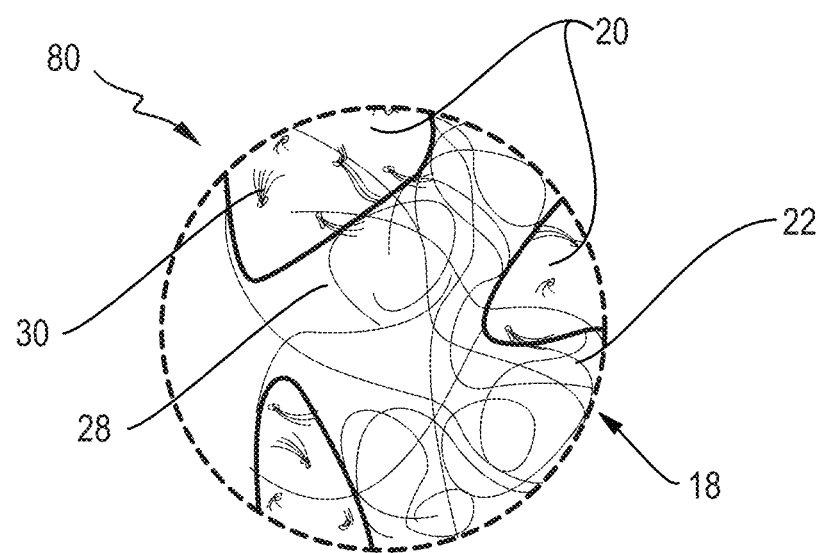
FIG. 8 is a magnified view of a portion of FIG. 5.

FIG. 8 is a zoomed in view of a portion of FIG. 5 indicated on FIG. 5 by a dotted line circle 80. As shown in FIG. 8, the heterogeneous mass 18 comprises discreet foam pieces 20 and enrobeable elements 30 in the form of fibers 22. Voids 28 containing gas are located between the fibers 22.

Figure 9:
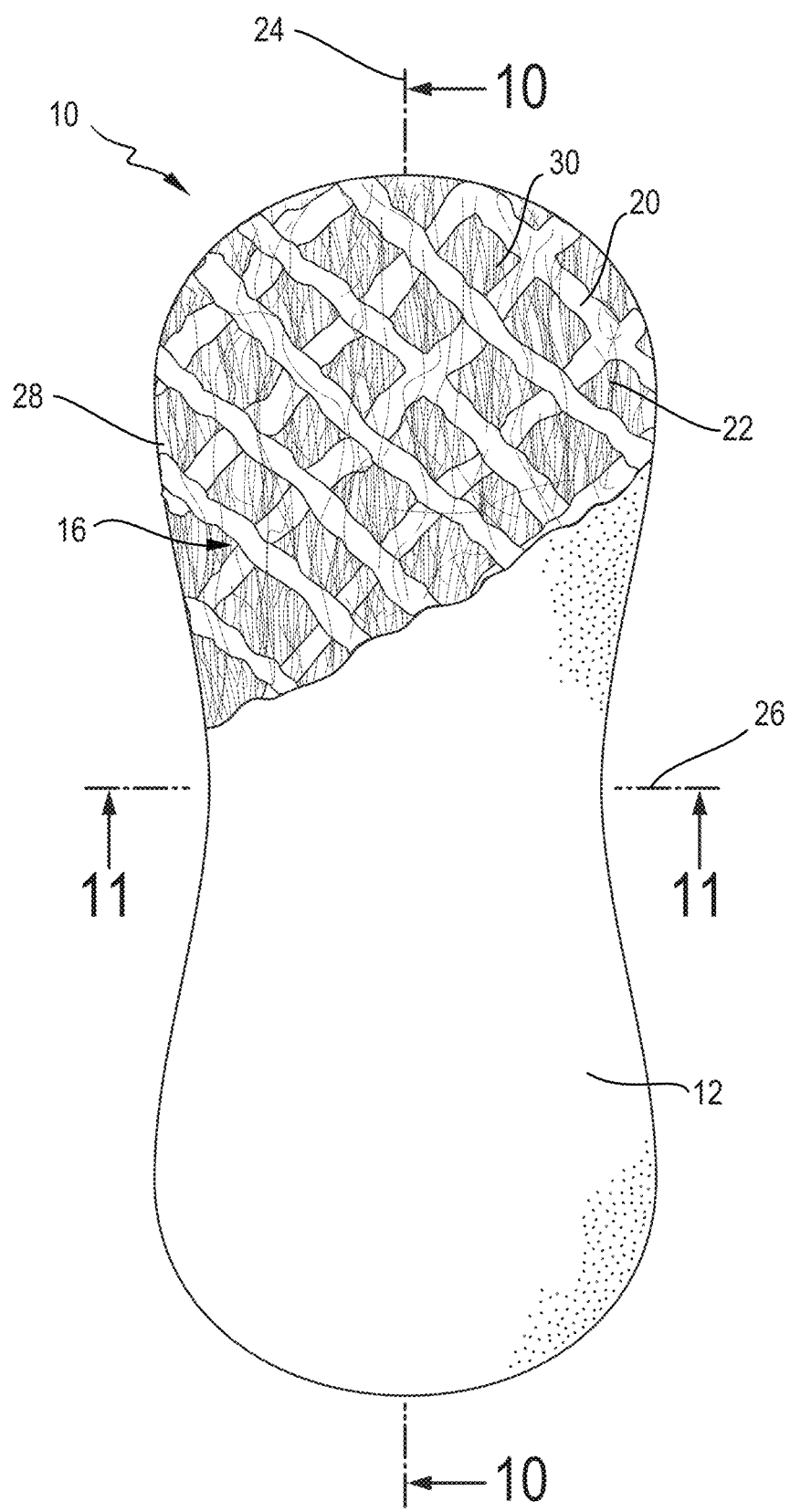
FIG. 9 is a top view of an absorbent article.

FIG. 9 is a plan view of a sanitary napkin 10 illustrating an embodiment of the invention. The sanitary napkin 10 comprises a topsheet 12, a backsheet (not shown), an absorbent core 16 located between the topsheet 12 and the backsheet, a longitudinal axis 24, and a transverse axis 26. The absorbent core 16 comprises of a heterogeneous mass 18 comprising elements 30 and one or more discrete foam pieces 20 that enrobe the at least one element 30 of the heterogeneous mass 18. As shown in FIG. 9, the elements 30 are fibers 22. A portion of the topsheet is cut out in order to show underlying portions. As shown in FIG. 9, the discrete foam pieces 20 may form a pattern, such as, for example, a checkerboard grid.

Figure 10:
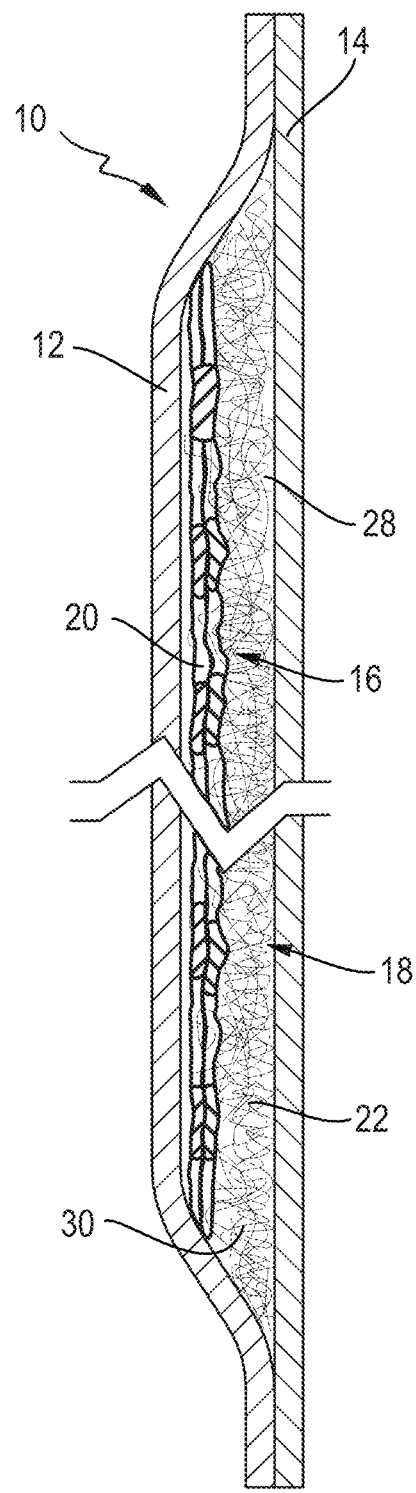
FIG. 10 is a cross section view of the absorbent article of FIG. 9 taken along line 10-10.
Figure 11:
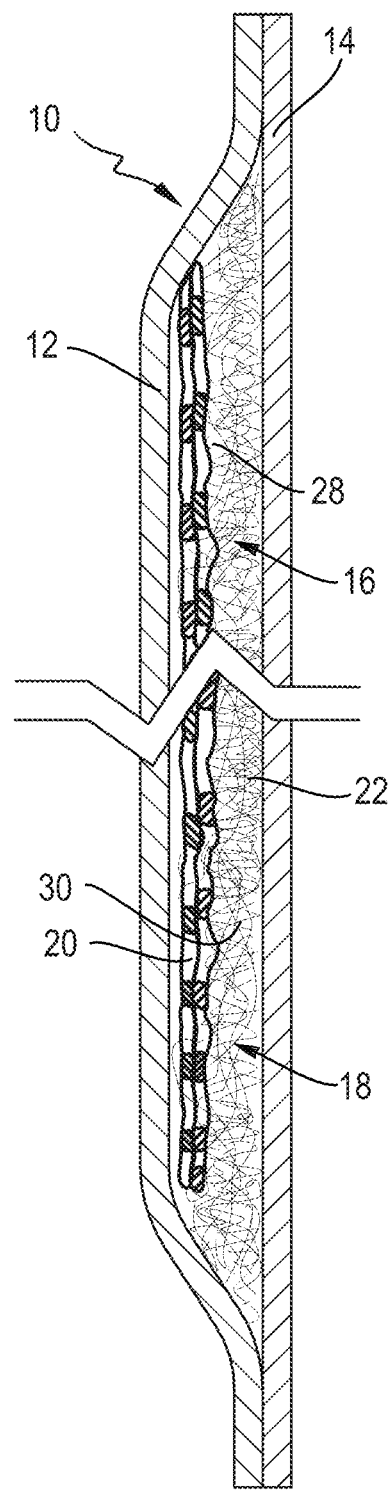
FIG. 11 is a cross section view of the absorbent article of FIG. 9 taken along line 11-11.

FIGS. 10 and 11 are cross sections of the pad shown in FIG. 9, cut through the 10-10 and 11-11 vertical planes, respectively. As may be seen in FIGS. 10 and 11, the absorbent core 16 is between the topsheet 12 and the backsheet 14. As shown in the embodiment of FIGS. 10 and 11, the discrete foam pieces 20 are spread out throughout the absorbent core and enrobe the elements 30 in the form of fibers 22 of the heterogeneous mass 18. Voids 28 containing gas are located between the fibers 22.

Figure 12:
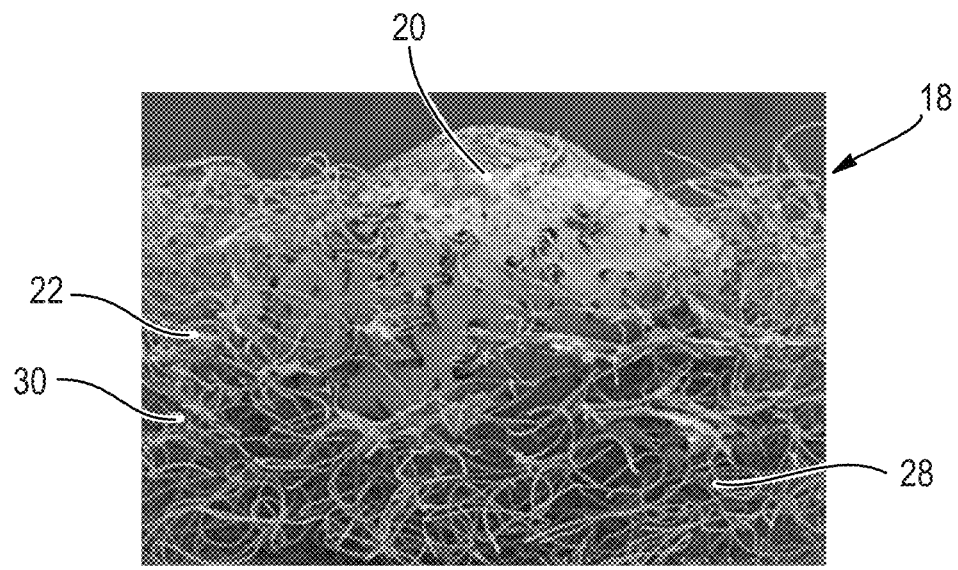
FIG. 12 is an SEM of a representative HIPE foam piece.

FIGS. 12 to 16 are SEM micrographs of HIPE foam pieces 20 intertwined within a heterogeneous mass 18 comprising nonwoven fibers 22. FIG. 12 shows a SEM micrograph taken at 15× magnification. As shown in FIG. 12, a discrete HIPE foam piece 20 and the elements 30 in the form of fibers 22 are intertwined. The HIPE foam piece 20 enrobes one or more of the fibers 22 of the heterogeneous mass 18. The fibers 22 of the heterogeneous mass 18 cross through the HIPE foam piece 20. Voids 28 containing gas are located between fibers 22.

Figure 13:
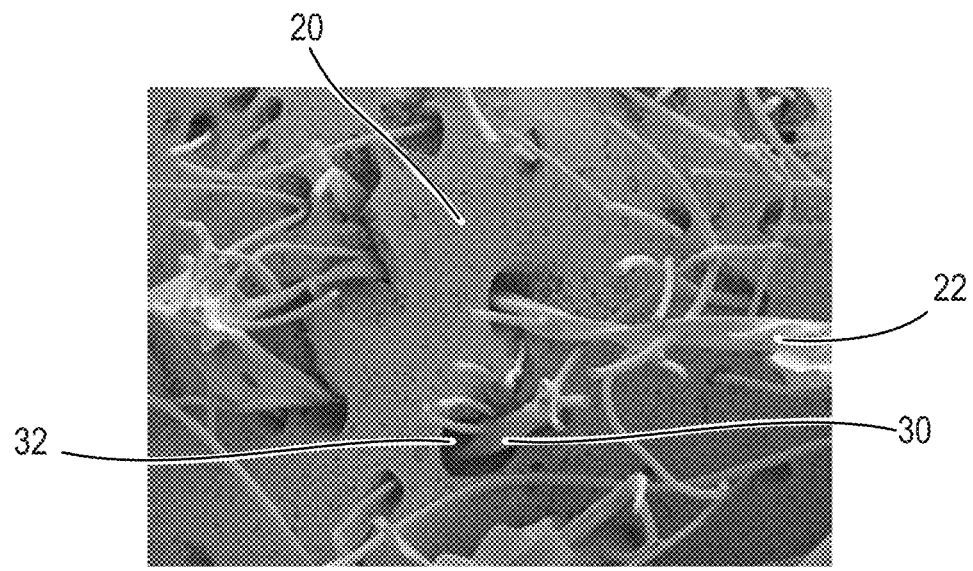
FIG. 13 is a magnified view of the SEM of FIG. 12.

FIG. 13 shows the absorbent core of FIG. 12 at a magnification of 50×. As shown in FIG. 13, the HIPE foam pieces 20 envelop a portion of one or more fibers 22 such that the fibers bisect through the HIPE foam pieces 20. The HIPE foam pieces 20 enrobe the fibers such that the pieces are not free to move about within the absorbent core. As shown in FIG. 13, vacuoles 32 may exist within the enrobing foam 20. Vacuoles 32 may contain a portion of the enrobeable element 30.

Figure 14:
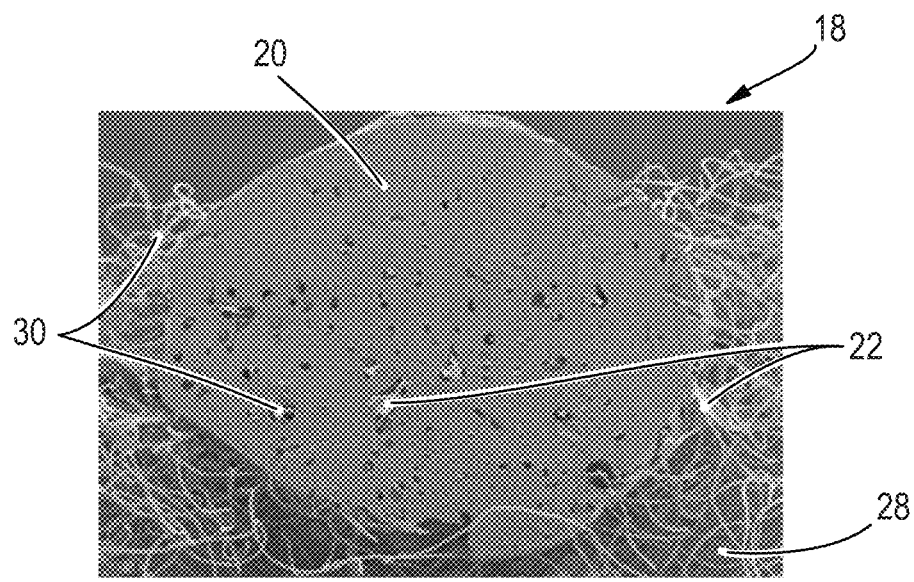
FIG. 14 is a cross section view of the SEM of FIG. 12.

FIG. 14 shows another SEM micrograph of a cross section of a discrete HIPE foam piece taken at 15× magnification. As shown in FIG. 14, the HIPE foam piece 20 may extend beyond the elements 30 of the heterogeneous mass 18 to form a portion of the outer surface of the heterogeneous mass 18. The HIPE foam pieces 20 enrobes one or more of the fibers 22 of the heterogeneous mass 18. The fibers of the absorbent core cross through the HIPE foam piece. Voids 28 containing gas are located between fibers 22.

Figure 15:
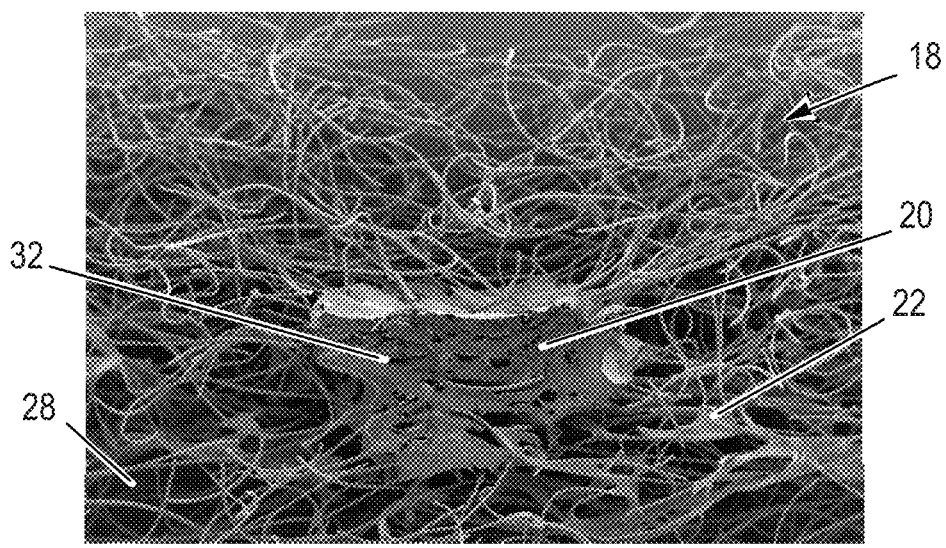
FIG. 15 is an SEM of a heterogeneous mass having an open-cell foam piece.

FIG. 15 shows another SEM micrograph of a heterogeneous mass 18 taken at a magnification of 18×. As shown in FIG. 15, the HIPE foam pieces 20 may be positioned below the outer surface of the heterogeneous mass 18 such that it does not form part of the outer surface of the heterogeneous mass 18 and is surrounded by fibers 22 and voids 28 containing gas. One or more vacuoles 32 may be formed within the foam piece 20.

Figure 16:
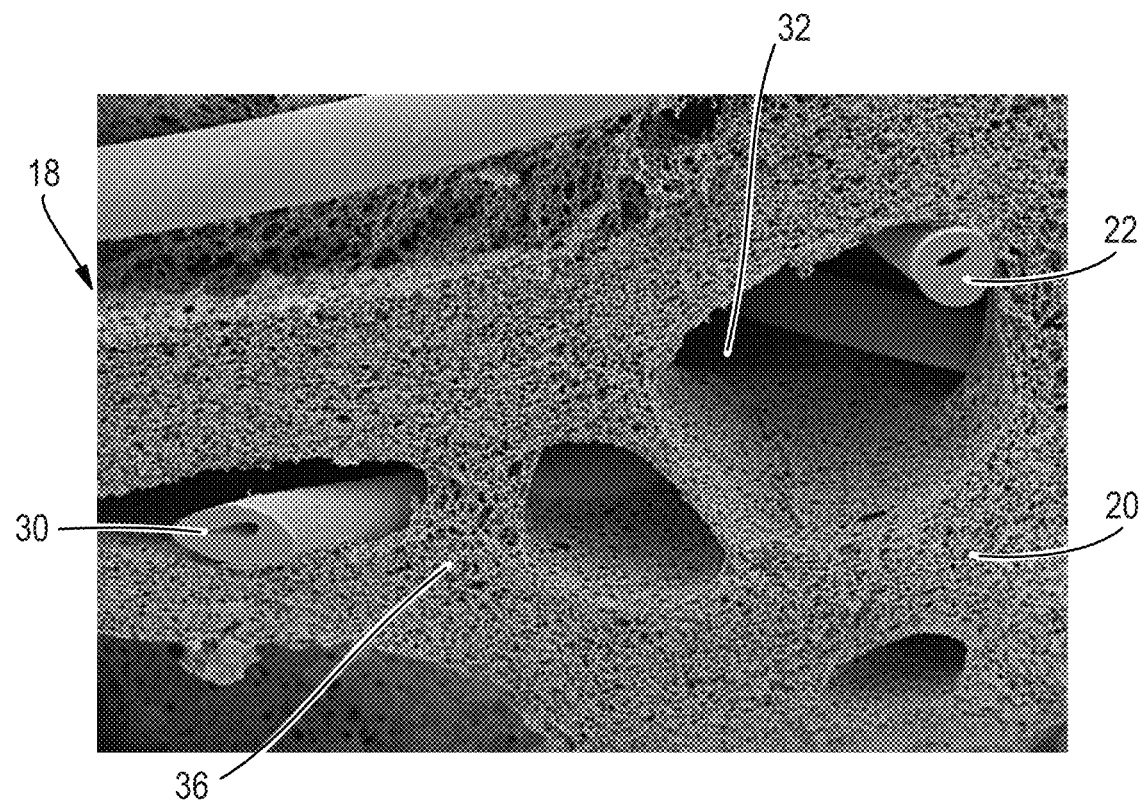
FIG. 16 is a magnified view of a portion of FIG. 15.

FIG. 16 shows a SEM micrograph of the heterogeneous mass of FIG. 15 taken at a magnification of 300×. As shown in FIG. 16, the heterogeneous mass 18 has an open-cell foam piece 20 that enrobes one or more enrobeable elements 30 in the form of fibers 22. As shown in FIG. 16, vacuoles 32 may exist within the enrobing foam 20. Vacuoles 32 may contain a portion of the enrobeable element 30. As shown in the figure, the vacuoles 32 have a cross-sectional surface area that is between 1.01 and 900,000,000 times the cross-sectional surface area of the fibers 22 or between 1.26 and 9,000,000 times the cross-sectional surface area of the cells 36 in the open-cell foam piece 20.

Figure 17:
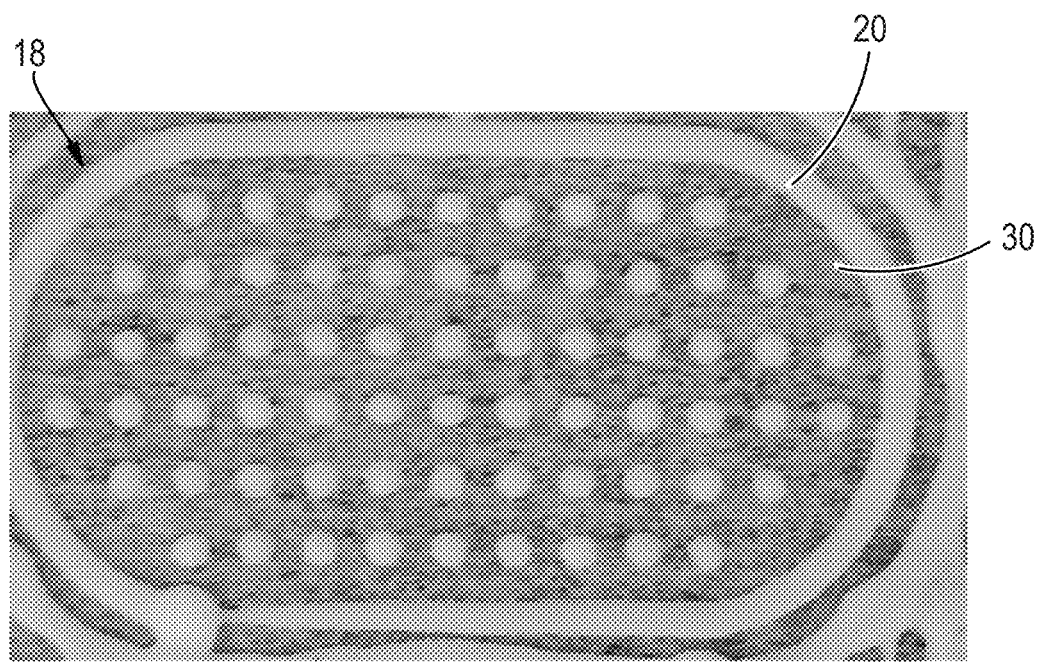
FIG. 17 is a top view image of a heterogeneous mass.

FIG. 17 is a photographic image of a heterogeneous mass 18 having enrobeable elements 30 comprising a nonwoven web and open-cell foam pieces 20 enrobing the enrobeable elements 30. As seen in the photographic image, the open-cell foam pieces are discrete along at least one of the lateral, longitudinal, or vertical axis of the heterogeneous mass. As seen in FIG. 17, the discrete open-cell foam pieces may form a pattern when viewed from above by a user.

Figure 18:
FIG. 18 is a cross section view of a heterogeneous mass.
Figure 19:
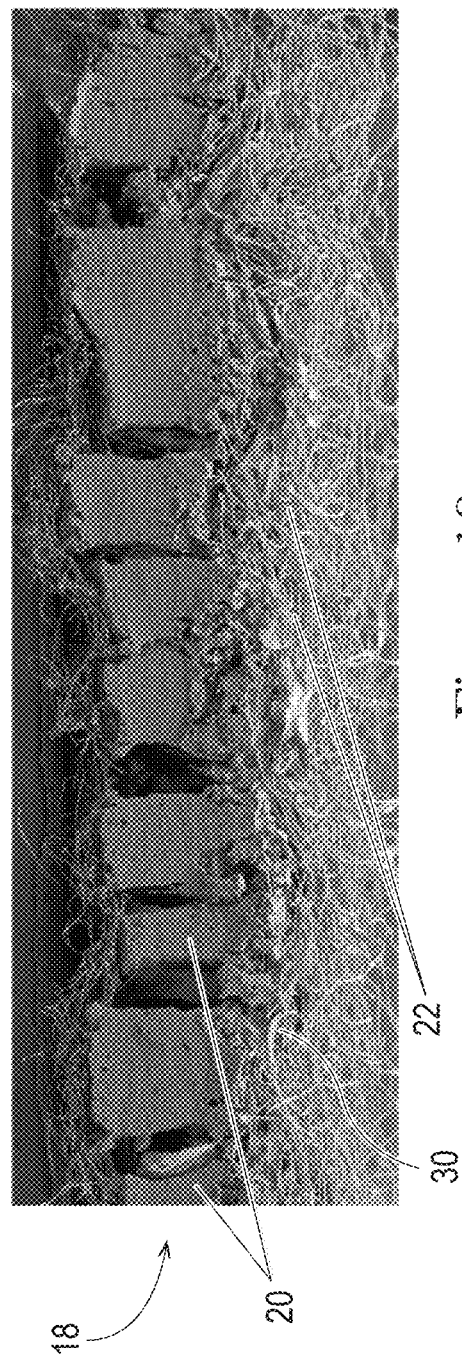
FIG. 19 is a cross-section view of a heterogeneous mass.

FIGS. 18 and 19 are SEM micrographs of the heterogeneous mass 18 at a magnification of 25×. The heterogeneous mass 18 comprises enrobeable elements 30 comprising a nonwoven web and open-cell foam pieces 20 enrobing the enrobeable elements 30. The open-cell foam pieces 20 of FIGS. 18 and 19 are discreet and spaced within the heterogeneous mass 18. As shown in FIG. 18, the use of discreet open-cell foam pieces 20 allows for flexibility in the heterogeneous mass 18 between the open-cell foam pieces 20. Enrobing the fibers with the open-cell foam pieces allows for immobilization of the open-cell foam within the heterogeneous mass. As shown in FIGS. 18-19, the open-cell foam pieces 20 are discreet in that they are discontinuous along the vertical and horizontal axis. This is demonstrated by having fibers or enrobeable elements above and below the open-cell foam along the vertical axis and by the discontinuity between the open-cell foam pieces along the horizontal axis which allows the heterogeneous mass to be flexible.

EXAMPLES

A. An absorbent structure comprising a single stratum exhibiting a Capillarity Work Potential greater than the Capillarity Work Potential trade-off Boundary.

B. The absorbent structure according to paragraph A, wherein the absorbent structure comprises a heterogeneous mass comprising enrobeable elements and one or more pieces of open-cell foam.

C. The absorbent structure according to paragraph A or B, wherein the absorbent structure exhibits a Capillary Work Potential of between 100 mJ/m$^2$ and 10,000 mJ/m$^2$ and a permeability between 10 Darcy and 10,000 Darcy.

D. The absorbent structure according to any of paragraphs A-C, wherein the absorbent structure exhibits a Capillary Work Potential of between 1,000 mJ/m$^2$ and 10,000 mJ/m$^2$ and a permeability between 10 Darcy and 10,000 Darcy.

E. The absorbent structure according to any of paragraphs A-D, wherein the absorbent structure exhibits a Capillary Work Potential of between 1,000 mJ/m$^2$ and 10,000 mJ/m$^2$ and a permeability between 10 Darcy and 1,000 Darcy.

F. The absorbent structure according to paragraph B, wherein the heterogeneous mass comprises at least 5% of discrete open cell foam pieces for a fixed volume.

G. The absorbent structure according to paragraph B, wherein the absorbent structure comprises less than 30% fibers by volume.

H. An absorbent article comprising the absorbent structure according to any of paragraphs A-G.

I. The absorbent structure according to paragraph B, wherein the enrobeable elements are selected from the group consisting of creped cellulose wadding, fluffed cellulose fibers, wood pulp fibers also known as airfelt, textile fibers, synthetic fibers, rayon fibers, airlaid, absorbent fibers thermoplastic particulates or fibers, tricomponent fibers, bicomponent fibers, tufts, and combinations thereof.

J. An absorbent structure according to any of paragraphs A-I, wherein the single stratum exhibits a permeability greater than the Capillarity Work Potential trade off Boundary for a given Capillary Work Potential.

Pore Volume Distribution Method

A porous material is comprised of effective and isolated pores of varying shape and size. Effective pores are those that are interconnected and eventually reach the surface of the structure. Those are the pores that contribute to the absorbent capacity of a given porous media. Isolated pores are those entirely surrounded by solid and therefore unable to contribute to absorbent properties directly. Pore Volume Distribution is a method that indirectly measures the estimated porosity of the effective pores and the Pore size distribution through a direct measurement of the quantity of fluid that enters pores at a given pressure.

The approach (i) applies pre-selected, incremental, pneumatic pressure (air) to a material that may absorb/desorb fluid through a fluid saturated pre-designed membrane and (ii) determines the incremental and cumulative quantity of fluid that is absorbed/desorbed by the material at each pressure. A weight is positioned on the material to ensure good contact between the material and membrane and to apply an appropriate mechanical confining pressure. Pore Volume Distribution for a sample may be measured between about 5 μm and 1000 μm.

A representative instrument is a one based on the TRI/Autoporosimeter (TRI/Princeton Inc. of Princeton, N.J.), in which the operation and data treatments is described in The Journal of Colloid and Interface Science 162(1994), pp. 163-170, incorporated here by reference.

Figure 21:
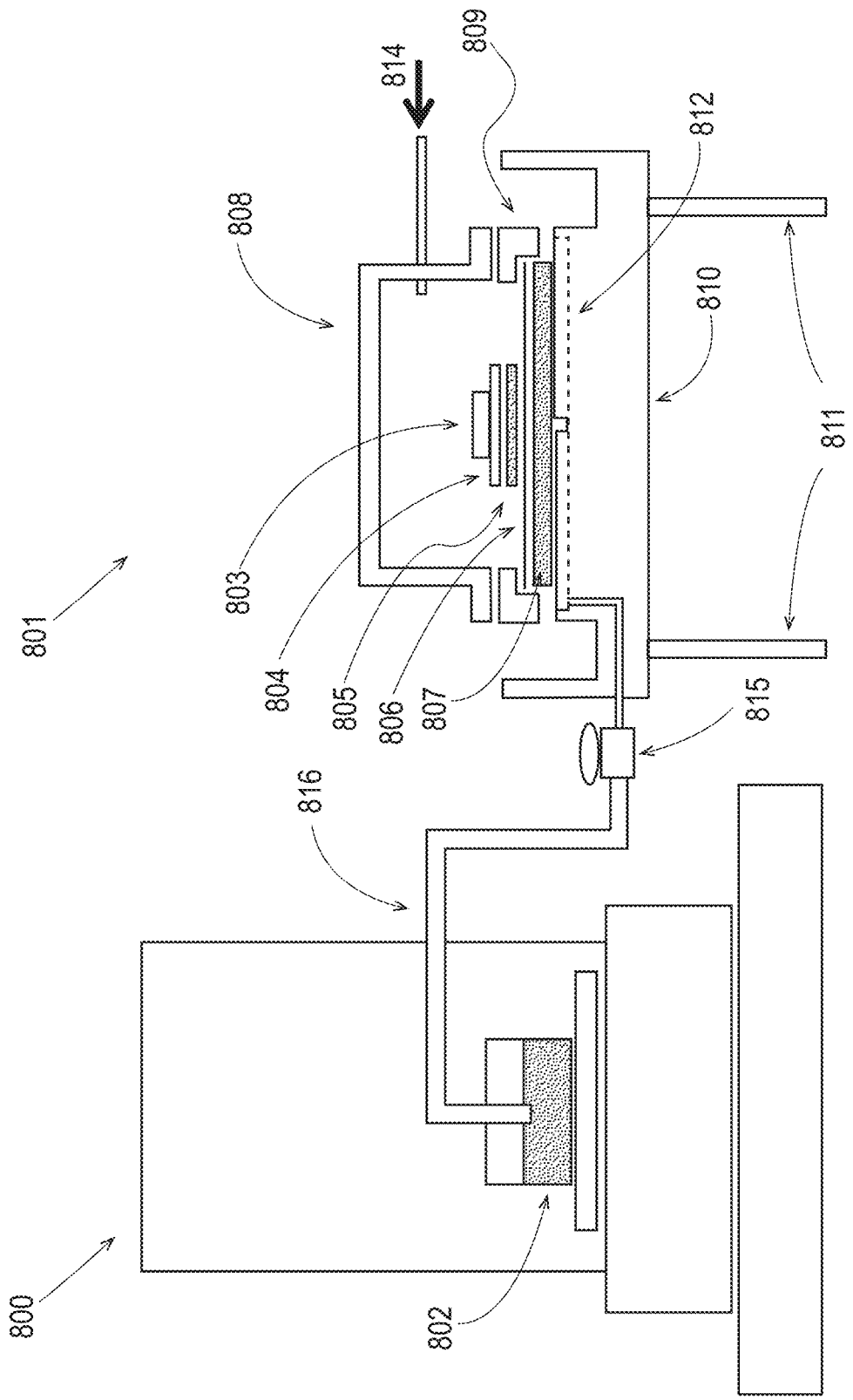
FIG. 21 is a representation of equipment used in testing pore volume.

A representation of the equipment is shown in FIG. 21 and consists of a balance 800 with fluid reservoir 801 which is in direct fluid communication with the sample 811 which resides in a sealed, air-pressurized sample chamber 810.

Determining the Pore Volume Uptake or Pore-Size Distribution involves recording the increment of liquid that enters or leaves a porous material as the surrounding air pressure is altered. A sample in the test chamber is exposed to precisely controlled changes in air pressure. As the air pressure increases or decreases, the void spaces or pores of the porous media de-water or uptake fluid, respectively. Total fluid uptake is determined as the total volume of fluid absorbed by the porous media.

Pore-Size Distribution can further be determined as the distribution of the volume of uptake of each pore-size range, as measured by the instrument at the corresponding pressure. The pore size is taken as the effective radius of a pore and is related to the pressure differential by the Laplace's equation below:

$$\Delta P = \frac{2\gamma \cos\alpha}{R}$$

where $\gamma$=liquid surface tension, and $\alpha$=contact angle

For this experiment we used Triton-X at 0.01% solution with surface energy, $\gamma$=31 dyne/cm and assumed perfect wetting ($\cos(\alpha)$=1). The automated equipment operates by precisely changing the test chamber air pressure in user-specified increments, either by decreasing pressure (increasing pore size) to cause fluid uptake by the porous media, or by increasing pressure (decreasing pore size) to drain the porous media. The liquid volume absorbed (drained) at each pressure increment yields the pore size distribution. The fluid uptake is the cumulative volume for all pores taken up by the porous media, as it progresses to saturation (e.g. all pores filled).

Experimental Conditions

Take a 9 cm diameter, 0.22 µm membrane filter (mixed cellulose esters, Millipore GSWP, EMD Millipore Corp., Billerica Mass.) by adhering the filter to a 9 cm diameter by 0.6 cm thick Monel porous frit 807 (available from Mott Corp, CT) using KRYLON® spray paint (FilmTools Gloss White Spray Paint #1501). Allow the frit/membrane to dry before use.

Fill the inner base 812 of the sample chamber with hexadecane (available from Sigma-Aldrich CAS #544-76-3). Place the frit 807 membrane side up onto the base of the sample chamber 810, and secure it into place with a locking collar 809. Fill the connecting tube 816, reservoir 802, and the frit 807 with hexadecane assuring that no bubbles are trapped within the connecting tube or the pores within the frit and membrane. Using the legs of the base 811, level the sample camber and align the membrane with the top surface of the fluid within the reservoir. Dye cut a specimen 5.5 cm square. Measure the mass of the specimen to the nearest 0.1 mg. A 5.5 cm square, Plexiglas cover plate 804 and confining weight 803 are selected to provide a confining pressure of 0.25 psi.

Place the top of the sample chamber 808 in place and seal the chamber. Apply the appropriate air pressure to the cell (connection 814) to achieve a 5 µm effective pore radius (based on Laplace's equation described earlier). Close the liquid valve 815. Open the sample chamber, place the specimen 805, cover plate 804 and confining weight 803 into the chamber onto the membrane 806 and seal the camber. Open the liquid valve 815 to allow free movement of liquid to the balance.

Progress the system through a sequence of pore sizes (pressures) as follows (effective pore radius in µm): 5, 10, 20, 30, 40, 50, 60, 70, 80, 90, 100, 120, 140, 160, 180, 200, 250, 300, 350, 400, 450, 500, 500, 550, 600, 700, 800, 1000, 800, 700, 600, 550, 500, 450, 400, 350, 300, 250, 200, 180, 160, 140, 120, 100, 90, 80, 70, 60, 50, 40, 30, 20, 10, 5, 10, 20, 30, 40, 50, 60, 70, 80, 90, 100, 120, 140, 160, 180, 200, 250, 300, 350, 400, 450, 500, 500, 550, 600, 700, 800, 1000. The sequence is progressed to the next radius when an equilibrium rate of less than 25 mg/min is measured at the balance.

In like fashion, measure the acquisition/drainage/acquisition cycle blank without a sample. Based on the incremental volume values, calculate the blank-corrected values for cumulative volume.

Cumulative Volume (mm³/mg)=[Specimen Fluid Uptake (mg)−Blank Fluid Uptake (mg)]/Density of Hexadecane (g/cm³)/Sample Mass (mg)

The Capillary Work Potential (CWP) is the work done by the sample normalized by the area of the specimen. The trapezoidal rule is used to integrate the ith pressure as a function of cumulative volume over n datapoints:

$$CWP\left[\frac{mJ}{m^2}\right] = \frac{W}{A_w} = \sum_{i=1}^{n} \frac{1}{2}\frac{m_w(CV_{i+1} - CV_i)(P_i + P_{i+1})}{A_w}\left(10^3\left[\frac{mJ}{J}\right]\right)$$

where
$m_w$=mass of web (mg)
CV=Cumulative Volume (m³/mg)
P=Air Pressure (Pa)
$A_w$=Area (m²)

Permeability (Darcy's) and Flow Rate (g/sec)

The Falling Hydro Head (FHH) Permeability test is a simple test that is widely used to assess permeability of a porous medium including soils, ground water and in absorbent materials. In the method the rate at which a column of liquid (of a known starting height) travels through a porous media is measured. The Falling Hydro Head Permeability value (k) is calculated from the saturated hydraulic conductivity (K), which describes the ease with which a fluid can move through pore spaces within a sample.

Sample Preparation:

Lay the article or layer of material to be assessed flat in a planar configuration on a surface, and using a die cutter, cut out a 30 mm diameter circular sample. Condition the sample at about 23° C.±2 C.° and about 50%±2% relative humidity for 2 hours prior to testing. All testing should be done under these same conditions. Prepare 10 replicate samples from substantially similar articles or layers of material for testing.

Testing Apparatus:

The testing apparatus is a cylindrical column composed of plexiglass tubing with an internal diameter of 138.2 mm and a height of 20 cm. The base is sealed with a recessed opening in the center that is 30 mm in diameter. The base of the recessed opening contains a porous stainless steel frit that will support the sample during testing but not significantly interfere with the fluid flow. A ring weight is used to seal the perimeter of the sample during testing, so that fluid will be restricted to only flowing through the sample. The ring weight has a 26 mm inner diameter opening with a 30 mm outer diameter to fit within the recessed opening at the base of the reservoir. A means of accurately measuring the height of the water column during the test is required, such as an ultrasonic height gauge mounted onto the top of the cylindrical reservoir, which is interfaced with a computer to allow for data logging over time during the experiment. A flow shut-off valve below the frit allows for the reservoir to be filled with fluid and then opened during testing.

Testing Procedure:

Place the cut sample flat onto the frit and put the ring weight on top of the sample. With the valve in the closed position, carefully fill the reservoir with de-ionized water to a height of 15 cm. Wait 5 minutes to allow the sample to fully saturate with fluid. Begin logging height data to the nearest 0.001 mm at a rate of a measurement every 0.1 seconds. Open the valve to allow the fluid to begin flowing through the sample. Continue to collect data for a sufficient length of time to produce a linear output of the water column height data over time. Repeat this procedure for all of the 10 replicate samples.

At the completion of the test, without undue delay, remove the saturated sample and measure its caliper. The sample caliper is measured using a height gauge with a 17.8 mm diameter foot applying a pressure of 0.1 psi. Record this value to the nearest 0.01 mm.

Additionally, the impact of the frit to the liquid flow rate needs to be assessed to be able to determine the permeability of the frit from the permeability of the sample. Repeat the test as described above without placing a sample on the frit.

Calculations:

Using the height versus time data that was collected during the experiment, plot the natural log of the initial height ($H_1$) divided by each of the subsequent heights ($H_2$) versus time. Calculate the slope of this line. Use this slope to calculate the saturated hydraulic conductivity (K) using the following equation:

$$K=(aL/At)\ln(H_1/H_2)$$

Where a is the cross sectional area of the column (m$^2$), L is the caliper of the saturated material (m), A is the cross sectional area of the sample available for flow (m$^2$), t is the time (s), $H_1$ is the initial water column height, and $H_2$ is the water column height at time (t).

Using the calculated saturated hydraulic conductivity (K) value, calculate the permeability (k) of the sample and convert the result to units of Darcys using the following equations:

$$k=K\mu/\rho g$$

$$k/9.87*10^{-13}=\text{Darcys}$$

Where K is the hydraulic conductivity (m/s), p is the fluid density (kg/m$^3$), g is the acceleration due to gravity (m/s$^2$), and μ is the fluid viscosity (Pa*s).

Using the permeability values calculated for the frit with the sample and frit alone, remove the permeability of the frit from the frit and sample value, and record this as the permeability of the sample. Repeat this procedure for all 10 replicates and calculate the statistical mean of all of the values and report as the Falling Hydro Head Permeability value (k) to the nearest 0.1 Darcys.

Punch Capacity Test Method

The Punch Capacity Test Method tests the uptake of fluid into a sample. The sample is supported in a basket with an open mesh screen at the bottom that is suspended from a top loading balance above a fluid delivery source. The test is started by allowing the fluid meniscus to touch the center of the sample to initiate capillary wicking. The wicking action (Uptake) continues until the sample reaches saturation (Equilibrium Capacity) or the test is interrupted or stopped at a pre-set time. Data points (i.e., weight and time) are collected and analyzed by a computer program. Results are reported as Uptake Rate in gram per sec. over time (plotted) and Equilibrium Capacity in grams fluid per gram of sample.

Procedure:

Allow all Standards and samples to equilibrate to the controlled temp. & humidity (Constant Temp. & Humidity Lab Conditioned to 23±2° C. (73±4° F.) temp., 50±4% Relative Humidity (R.H.)) for at least two (2) hours prior to testing.

Finished Product Theoretical Capacity Sample Preparation:

Remove test pad from polybag/carton and fold & wrap (F&W) pouch. With release paper (RP) in place, cut sample 'as is' leaving the release paper in place during fluid loading to prevent adhesive from sticking to the basket. Note: Some samples have F&W and RP as one integral piece. In this case, open the F&W pouch and leave F&W/RP in place to cut samples out.

Using the hydraulic press and the circular rule die, prepare Punch HGW sample(s) by cutting a 25.7 cm$^2$ (2¼ in dia.) sample from the center of the test pad.

Pre-Test Finished Product and Raw Material Basis Weight and Density Determination:

$$\text{LENGTH}(L)\text{ cm}*\text{WIDTH}(W)\text{ cm}=\text{AREA cm}^2 \quad \text{Area:}$$

Calculate the area of the test sample (e.g., L*W=Area cm$^2$—or—if using the std. circular die use 25.7 cm$^2$ (3.98 in$^2$))

$$\text{DRY WT. g/AREA cm}^2 \quad \text{Basis Weight:}$$

Weigh the sample to the nearest 0.01 grams using a 2 decimal-place analytical balance. Record the weight as g/in$^2$ or g/25.7 cm$^2$.

$$\text{DRY WT. g/AREA cm}^2*\text{CALIPER cm} \quad \text{Density:}$$

Determine the thickness of the sample to the nearest 0.01 inch or 0.025 cm using a caliper gauge. Multiply the thickness by the area (e.g., 3.98 in$^2$*0.75 in=2.99 in$^3$ or 25.7 cm$^2$*1.88 cm=48.19 cm$^3$). Record the weight as g/in$^3$ or g/48.19 cm$^3$.

Fluid Uptake Testing Protocol:

1. Place the pre-weighed (dry) finished product sample punch (topsheet side down) in the center of the sample holder basket over the opening at the bottom of the basket. Snap the top of the basket back into place and lock it down using the two locks on either end of the sample basket.
2. Hang the sample basket from the bottom of the balance.
3. Place the static weight for the desired confining pressure (0.06 psi or 0.25 psi load) on top of the sample covering the sample completely, and then level the sample basket using the level bubbles on the top of the basket as a guide.
4. Fill the lower reservoir with test fluid and start the peristaltic pump to re-circulate fluid throughout the HGW system and to keep the (suspension) test fluid from separating. Set the pump's flow rate to an approximate setting of "2" and adjust the speed up or down as necessary to prevent over-agitating the fluid and allow fluid to completely fill the upper reservoir and all of the tubing leading into the fluid loading system. Carefully add more test fluid to the lower reservoir via the upper reservoir container (fluid will drain down through the overflow tubing into the lower reservoir), as needed to keep the system full during testing of samples.
5. Using the micro-slide adjustment on the upper reservoir, make sure the test fluid's meniscus is approximately 5 mm below the top of the fluid delivery tube's tip opening.
6. Tare the HGW balance.

7. Using the lab jack, raise the fluid loading column's tube tip so that it is centered underneath the sample basket's screen opening at the bottom, and set the gap distance at approximately 3 mm from the sample's topsheet surface that is exposed at the opening in the screen.
8. Using the micro-slide adjustment on the upper reservoir, adjust the meniscus so that the test fluid meniscus bridges (touches) the sample. Check to be sure that the tip of the fluid delivery column or the air and fluid delivery tubing are not hanging-up on the basket, or that the basket isn't tared prior to starting test—re-adjust positioning, if needed. And, re-tare the balance to clear the error.
9. Launch the BalanceLink software and the Excel spreadsheet template on your PC. Fill-in all of the test description data entry fields on the template (sample description, operator's name, date, etc.). Insert the cursor into the first data cell for capturing the sample's uptake weight gain at Zero (0) time on the spreadsheet template.
10. Using the pre-set "Hot Key" (e.g., [PrntScrn] or [F6]) START BalanceLink data logger to acquire the uptake data.
11. Continue to monitor the meniscus fluid bridging to ensure the sample is not touching the fluid delivery tip due to sample wet collapse or swelling, and to be sure the basket or any tubing hasn't shifted out of position during the test duration—carefully re-adjust height or basket position, if it does shift or starts to touch.

Run the first sample 'open' to determine the time required to reach equilibrium capacity.

Note: Punch testing of raw materials and test pads take ~5 to 30 min. to run. Some samples may run longer depending upon materials to be tested.

12. After reaching equilibrium capacity (noting three or more consecutive 0.01 grams Rate of Uptake results in the Rate column on the spreadsheet), STOP data acquisition using the "Hot Key". Turn off the air supply or remove the confining weight and remove the sample from the basket
13. Verify and record sample weight gain (wet-dry wt.=wt. gain or Equilibrium Capacity) using a top loading balance. Start next sample.
14. Pre-weigh a 7-ply stack of 4 cm×4 cm Ahlstrom 989 filter paper.
15. $1^{st}$ Rewet: Place the pre-weighed pick-up paper on top of the saturated sample and apply the 0.25 psi load for 30 sec using either the 0.25 psi static wt. or the pneumatic pressure application device. At the end of the 30 sec interval, remove and reweigh the filter paper stack and calculate the difference between the Wet Pick-Up Paper weight (g) minus the Dry Pick-Up Paper weight (g) to determine the amount of fluid that rewet (squeezed-out) back up through the topsheet.

Report this 'squeeze-out' as Rewet at the 0.25 psi load.

16. Pre-weigh a second, fresh 7-ply stack of Ahlstrom 989 pick-up paper.
17. $2^{nd}$ Sequential Rewet: Place the pick-up paper stack on top of the saturated sample and apply the 1.0 psi load for 15 sec using either the 1.0 psi static wt. or the pneumatic pressure application device. At the end of the 15 sec interval, remove and reweigh the filter paper stack and calculate the difference between the Wet Pick-Up Paper weight (g) minus the Dry Pick-Up Paper weight (g) to determine the amount of fluid that rewet (squeezed-out) back up through the topsheet.

Report this 'squeeze-out' as Rewet at the 1.0 psi load.

18. Weigh the pad after doing the 0.25 psi and 1.0 psi sequential blots to determine the sample's Retained Capacity (g). Subtract the Wet Pad weight minus the Dry Pad weight (g) to determine the sample's Retained Capacity (g).

Report this as Retained Capacity and show results to the nearest 0.01 g.

Plot data accordingly for the Contiguous Mean RATE OF UPTAKE (gm/sec) where TIME (sec) as the X-axis and FLUID UPTAKE (gm) as the Y-axis.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent structure comprising a single stratum, the structure comprising a heterogeneous mass, the heterogeneous mass comprising a layer of open cell foam broken into a plurality of discrete open cell foam pieces enrobing a plurality of fibers, the structure exhibiting a Capillarity Work Potential greater than the Capillarity Work Potential trade-off Boundary.

2. The absorbent structure of claim 1, wherein the absorbent structure exhibits a Capillary Work Potential of between 100 mJ/m$^2$ and 10,000 mJ/m$^2$ and a permeability between 10 Darcy and 10,000 Darcy.

3. The absorbent structure of claim 1, wherein the absorbent structure exhibits a Capillary Work Potential of between 1,000 mJ/m$^2$ and 10,000 mJ/m$^2$ and a permeability between 10 Darcy and 10,000 Darcy.

4. The absorbent structure of claim 1, wherein the absorbent structure exhibits a Capillary Work Potential of between 1,000 mJ/m$^2$ and 10,000 mJ/m$^2$ and a permeability between 10 Darcy and 1,000 Darcy.

5. The absorbent structure of claim 1, wherein the heterogeneous mass comprises at least 5% of discrete open cell foam pieces for a fixed volume.

6. The absorbent structure of claim 1, wherein the absorbent structure comprises less than 30% fibers by volume.

7. An absorbent article comprising the absorbent structure according to claim 1.

8. The absorbent structure of claim 1, wherein the enrobeable elements are selected from the group consisting of creped cellulose wadding, fluffed cellulose fibers, wood pulp fibers also known as airfelt, textile fibers, synthetic fibers, rayon fibers, airlaid, absorbent fibers thermoplastic particulates or fibers, tricomponent fibers, bicomponent fibers, tufts, and combinations thereof.

9. An absorbent structure comprising a single stratum, the structure comprising a heterogeneous mass, the heterogeneous mass comprising a layer of open cell foam broken into a plurality of discrete open cell foam pieces enrobing a plurality of fibers, the structure exhibiting a permeability greater than the Capillarity Work Potential trade-off Boundary for a given Capillary Work Potential.

10. The absorbent structure of claim 9, wherein the heterogeneous mass comprises at least 5% of discrete open cell foam pieces for a fixed volume.

11. The absorbent structure of claim 9, wherein the enrobeable elements are selected from the group consisting of creped cellulose wadding, fluffed cellulose fibers, wood pulp fibers also known as airfelt, textile fibers, synthetic fibers, rayon fibers, airlaid, absorbent fibers thermoplastic particulates or fibers, tricomponent fibers, bicomponent fibers, tufts, and combinations thereof.

12. The absorbent structure of claim 9, wherein the enrobeable elements are selected from the group consisting of a nonwoven, a fibrous structure, an air-laid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are alwed combinations thereof.

13. The absorbent structure of claim 9, wherein the discrete open cell foam pieces comprise HIPE foam.

14. The absorbent structure of claim 9, wherein the absorbent structure exhibits a Capillary Work Potential of between 1,000 mJ/m$^2$ and 10,000 mJ/m$^2$ and a permeability between 10 Darcy and 1,000 Darcy.

15. An absorbent structure comprising a single stratum, the structure comprising a heterogeneous mass, the heterogeneous mass comprising a layer of open cell foam broken into a plurality of discrete open cell foam pieces enrobing a plurality of fibers, structure exhibiting a Capillarity Work Potential for a fixed permeability that is greater than the Capillarity Work Potential trade-off Boundary and less than 20 times the Capillary Work Potential trade-off and a permeability greater than the Capillarity Work Potential trade-off Boundary for a given Capillary Work Potential.

16. The absorbent structure of claim 15, wherein the absorbent structure exhibits a Capillary Work Potential of between 1,000 mJ/m$^2$ and 10,000 mJ/m$^2$ and a permeability between 10 Darcy and 1,000 Darcy.

17. The absorbent structure of claim 15, wherein the absorbent structure exhibits a Capillary Work Potential of between 1,000 mJ/m$^2$ and 10,000 mJ/m$^2$ and a permeability between 10 Darcy and 1,000 Darcy.

* * * * *